United States Patent
Hatano et al.

(10) Patent No.: US 10,502,796 B2
(45) Date of Patent: Dec. 10, 2019

(54) MAGNETOMETER

(71) Applicant: RENESAS ELECTRONICS CORPORATION, Tokyo (JP)

(72) Inventors: Yuji Hatano, Tokyo (JP); Takashi Yoshino, Tokyo (JP)

(73) Assignee: RENESAS ELECTRONICS CORPORATION, Tokyo (JP)

( * ) Notice: Subject to any disclaimer, the term of this patent is extended or adjusted under 35 U.S.C. 154(b) by 0 days.

(21) Appl. No.: 15/432,250

(22) Filed: Feb. 14, 2017

(65) Prior Publication Data

US 2017/0234941 A1    Aug. 17, 2017

(30) Foreign Application Priority Data

Feb. 16, 2016    (JP) ................................. 2016-026993

(51) Int. Cl.
  *G01R 33/032*    (2006.01)
  *G01R 33/12*    (2006.01)
  *A61B 5/00*    (2006.01)

(52) U.S. Cl.
  CPC ....... *G01R 33/032* (2013.01); *G01R 33/1284* (2013.01); *A61B 5/0071* (2013.01)

(58) Field of Classification Search
  CPC .............. G01R 33/032; G01R 33/1284; A61B 5/04008; A61B 5/0071
  See application file for complete search history.

(56) References Cited

U.S. PATENT DOCUMENTS

| | | | |
|---|---|---|---|
| 2010/0321117 A1* | 12/2010 | Gan | G04F 5/145 331/3 |
| 2011/0062957 A1* | 3/2011 | Fu | G01N 24/088 324/307 |

(Continued)

FOREIGN PATENT DOCUMENTS

| | | |
|---|---|---|
| CN | 105137371 A | 12/2015 |
| JP | 2014-517322 A | 7/2014 |
| WO | 2015/107907 A1 | 7/2015 |

OTHER PUBLICATIONS

D. LeSage et al., "Efficient photon detection from color centers in a diamond optical waveguide," Physical Review B 85, 121202(R) (2012).

(Continued)

*Primary Examiner* — Kenneth J Malkowski
(74) *Attorney, Agent, or Firm* — McDermott Will & Emery LLP

(57) ABSTRACT

A magnetometer includes a diamond sensor, an excitation light source, a diamond sensor case, and a photodiode. The excitation light source irradiates the diamond sensor case with excitation light. In the diamond sensor case, a reflection film which reflects excitation light is formed on either a front surface or an inner surface, and the diamond sensor is stored. The photodiode detects intensity of fluorescence generated from the diamond sensor. The diamond sensor case includes a fluorescence output window and an excitation-light reception window. Fluorescence generated by the diamond sensor is output through the fluorescence output window. Excitation light emitted by the excitation light source is received through the excitation-light reception window. The photodiode is provided on a side of a second surface opposite to a first surface which is a magnetism measurement surface of the diamond sensor.

13 Claims, 22 Drawing Sheets

(56) References Cited

U.S. PATENT DOCUMENTS

| | | | | |
|---|---|---|---|---|
| 2014/0166904 A1* | 6/2014 | Walsworth | ......... | G01N 21/6489 250/459.1 |
| 2014/0247094 A1* | 9/2014 | Englund | ............ | G01R 33/1284 331/94.1 |
| 2016/0334474 A1* | 11/2016 | Hatano | ................... | C30B 25/02 |

OTHER PUBLICATIONS

Japanese Notification of Reasons for Refusal issued in corresponding Japanese Patent Application No. 2016-026993, dated Sep. 24, 2019, with English translation.

* cited by examiner

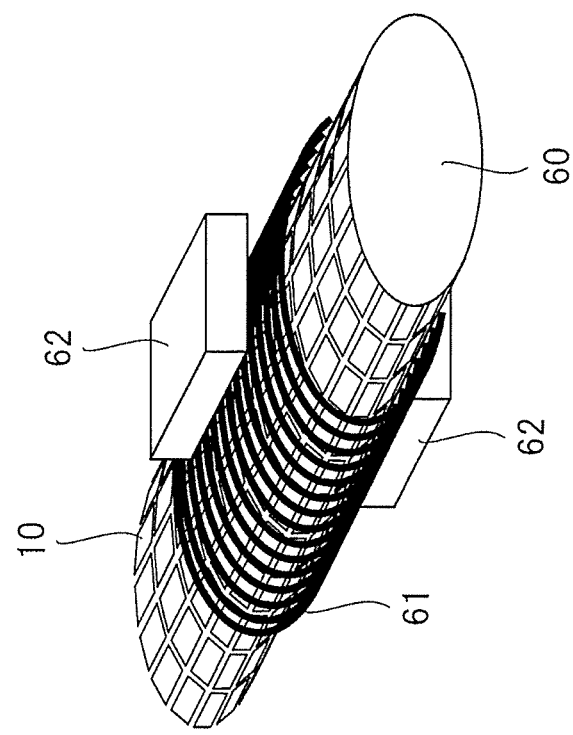
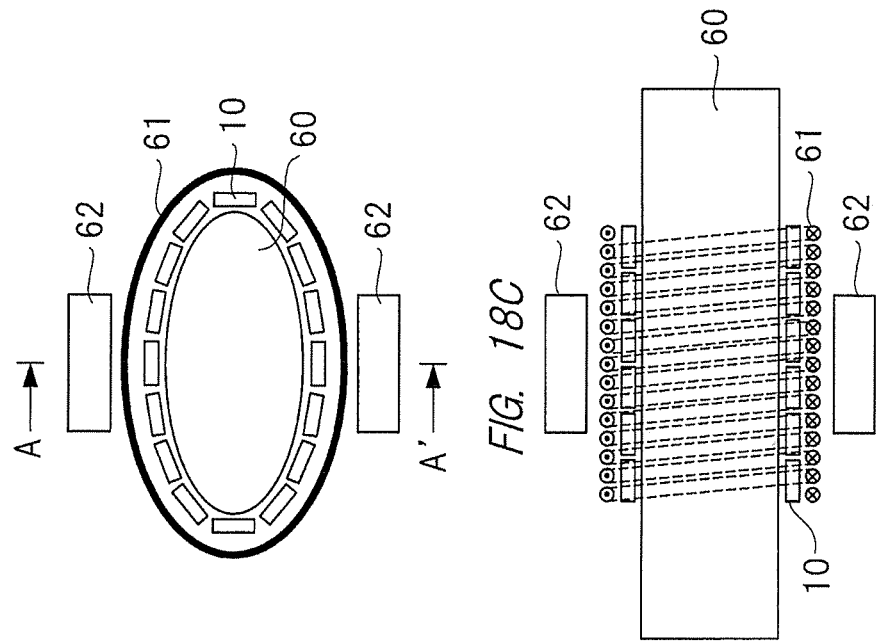
FIG. 18A
FIG. 18B
FIG. 18C

MAGNETOMETER

CROSS-REFERENCE TO RELATED APPLICATION

The present application claims priority from Japanese Patent Application No. 2016-026993 filed on Feb. 16, 2016, the content of which is hereby incorporated by reference into this application.

TECHNICAL FIELD OF THE INVENTION

The present invention relates to a magnetometer, and particularly relates to an effective technique in miniaturizing a highly-sensitive magnetic sensor using nitrogen-vacancy centers of a diamond crystal.

BACKGROUND OF THE INVENTION

For a highly-sensitive magnetometer which is operable at a room temperature, a diamond crystal including nitrogen-vacancy centers (NV centers) has been proposed (see, for example, D. Sage et al., "Efficient photon detection from color centers in a diamond optical waveguide" PHYSICAL REVIEW B 85, 121202(R) (2012) (Non-Patent Document 1)).

The Non-Patent Document 1 discloses that, by detecting fluorescence generated from a diamond crystal while irradiating the diamond crystal with excitation light of a green laser and a microwave pulse train in a controlled cycle, an alternating-current magnetic field corresponding to the cycle can be measured.

It further discloses that the sensitivity improvement can be achieved by collecting also a part of the fluorescence radiated from a periphery of the diamond crystal in various directions in addition to the commonly-performed detection of a part of the fluorescence reflected in an incidence direction of excitation light.

SUMMARY OF THE INVENTION

According to the Non-Patent Document 1 described above, while green excitation light is incident onto one surface of the diamond crystal from a green-laser light source via a dichroic mirror, fluorescence which is reflected from the surface in an incidence direction of the excitation light is separated from the excitation light by the dichroic mirror, and then the fluorescence is detected in a photodiode via low-pass filters.

At the same time, fluorescence which is radiated from four side surfaces of the diamond crystal, which are orthogonal to the incidence direction of the excitation light, is also detected by the low-pass filters and the photodiodes which are provided for respective surfaces. In this manner, fluorescence collection efficiency is enhanced, so that the sensitivity improvement can be achieved.

Further, the low-pass filters and the photodiodes are respectively provided for five surfaces in total. The dichroic mirror is also provided for one of the surfaces. Because of large volumes of these optical components, a volume of a whole magnetometer is increased. This causes a problem of increasing a size of various kinds of devices formed by using the magnetometer.

A magnetometer according to one embodiment includes a diamond sensor, an excitation light source, a diamond sensor case, and a fluorescence intensity detecting unit. The diamond sensor includes a plurality of nitrogen-vacancy centers.

The excitation light source irradiates the diamond sensor case with excitation light. In the diamond sensor case, a reflection film which reflects the excitation light is formed on either a front surface or an inner surface, and the diamond sensor is stored. The fluorescence intensity detecting unit detects intensity of fluorescence generated from the diamond sensor case.

The diamond sensor case has a first window and a second window. Fluorescence generated by the diamond sensor is output through the first window. Excitation light emitted by the excitation light source is received through the second window. Further, the fluorescence intensity detecting unit is provided on a side of a second surface opposite to a first surface which is a magnetism measurement surface of the diamond sensor.

In particular, the second window is formed at a position where at least one side surface of the diamond sensor is irradiated with the excitation light. The excitation light source irradiates the second window with the excitation light.

Further, the magnetometer includes a control circuit which controls operations of the excitation light source. When a plurality of second windows are provided, the control circuit controls the excitation light source so that each of the plurality of second windows is individually irradiated with excitation light.

According to the above-described one embodiment, miniaturization of a magnetometer can be achieved.

BRIEF DESCRIPTIONS OF THE DRAWINGS

FIG. 18A is an explanatory drawing showing an example of a health care device using a magnetometer according to an eighth embodiment;

FIG. 18B is an explanatory drawing showing the example of the health care device using the magnetometer according to the eighth embodiment;

FIG. 18C is an explanatory drawing showing the example of the health care device using the magnetometer according to the eighth embodiment;

DESCRIPTIONS OF THE PREFERRED EMBODIMENTS

Figure 1:
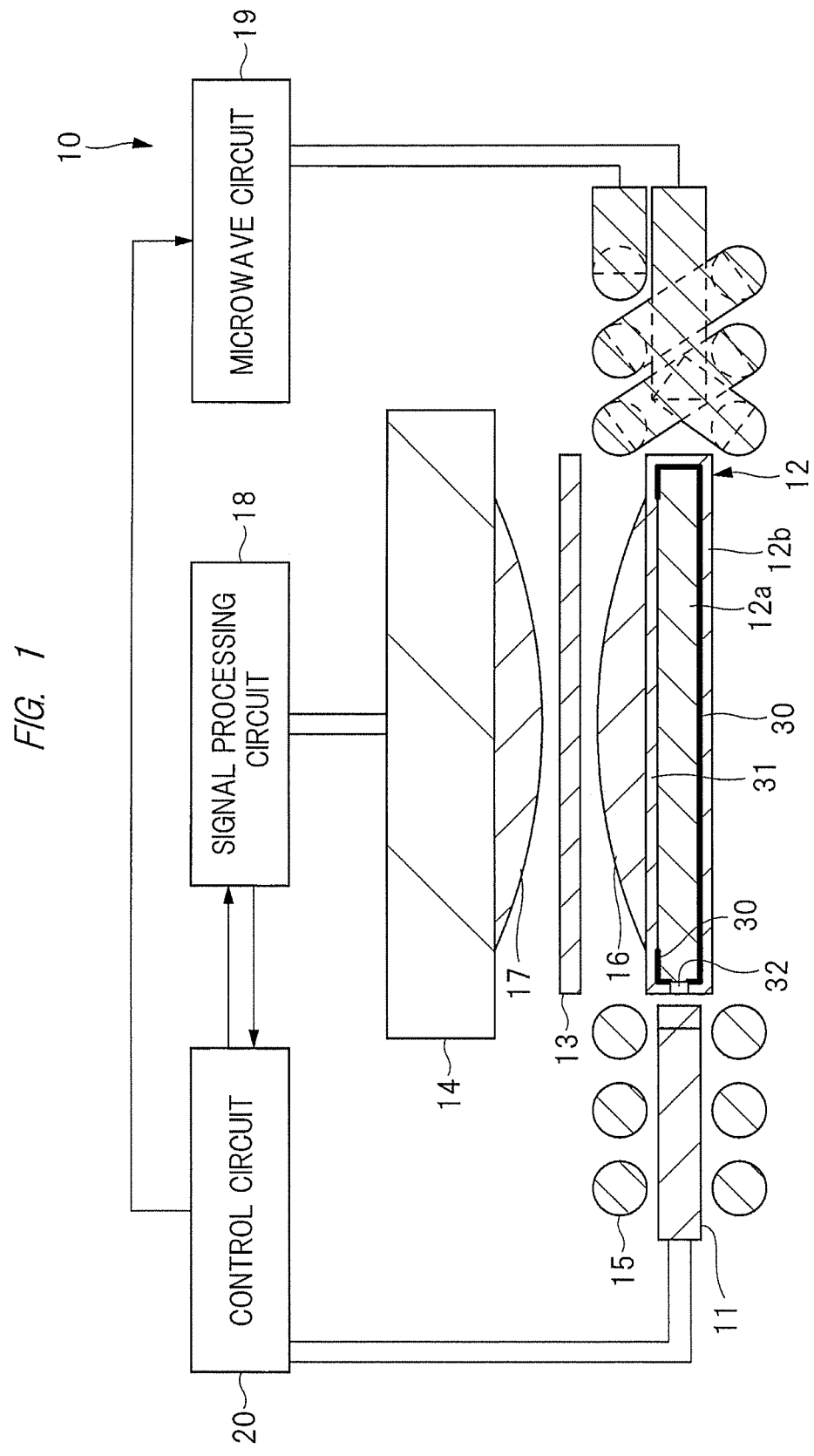
FIG. 1 is an explanatory drawing showing an example of a structure of a magnetometer according to a first embodiment.

In the embodiments described below, the invention will be described in a plurality of sections or embodiments when required as a matter of convenience. However, these sections or embodiments are not irrelevant to each other unless otherwise stated, and the one relates to the entire or a part of the other as a modification example, details, or a supplementary explanation thereof.

Also, in the embodiments described below, when referring to the number of elements (including number of pieces, values, amount, range, and the like), the number of the elements is not limited to a specific number unless otherwise stated or except the case where the number is apparently limited to a specific number in principle, and the number larger or smaller than the specified number is also applicable.

Further, in the embodiments described below, it goes without saying that the components (including element steps) are not always indispensable unless otherwise stated or except the case where the components are apparently indispensable in principle.

Similarly, in the embodiments described below, when the shape of the components, positional relation thereof, and the like are mentioned, the substantially approximate and similar shapes and the like are included therein unless otherwise stated or except the case where it is conceivable that they are apparently excluded in principle. The same goes for the numerical value and the range described above.

Also, components having the same function are denoted by the same reference characters throughout the drawings for describing the embodiments in principle, and the repetitive description thereof will be omitted. In addition, hatching is used even in a plan view so as to make the drawings easy to see.

<Overview>

In a magnetometer according to one embodiment, a photodiode is disposed on a back surface opposite to a main surface, which is a magnetism measurement surface of a plate-shaped diamond sensor case in which a plate-shaped diamond sensor is stored, with a low-pass filter interposed therebetween. In this regard, the main surface is the magnetism measurement surface of the diamond sensor and serves as a first surface. Also, the back surface serves as a second surface.

Lenses are disposed between the low-pass filter and the second surface of the diamond sensor and between the low-pass filter and the photodiode, respectively. A reflection film is provided on an inner surface of the diamond sensor case. In the diamond sensor case, a window through which fluorescence is output is provided in a portion where the second surface of the diamond sensor and the lens come into contact with each other. Also, a window through which excitation light from an excitation light source is received is provided in a side surface of the diamond sensor case.

The reflection film is a metal film, and is so designed as to have a thickness which is smaller than a skin-effect depth at a frequency of a microwave and is larger than a skin-effect depth at a frequency of light. For example, the thickness is set at about 300 nm for titanium, and the thickness is set at about 100 nm for aluminum.

A microwave coil is provided around the diamond sensor case. The microwave coil applies a microwave of a frequency corresponding to a static magnetic field at a position of the diamond sensor. It is designed such that a magnetic field generated by the microwave coil is perpendicular to the main surface of the diamond sensor.

Since diamond has a high refractive index (n=2.4), incident excitation light is likely to be multi-reflected within a crystal, but it is possible to enhance excitation efficiency by storing the diamond sensor in the diamond sensor case having the reflection film provided therein. A part of the excitation light is output via the lens, but is reflected by the low-pass filter, and most of the excitation light is returned to the diamond sensor case.

On the other hand, fluorescence which is output from NV centers irradiated with the excitation light is also multi-reflected and confined in the diamond sensor case. A part of the fluorescence is output to the photodiode via the lens and the low-pass filter.

Since the thickness of the reflection film is larger than the skin-effect depth at the frequency of light, most of light is reflected. On the other hand, since the thickness of the reflection film is smaller than the skin-effect depth at the frequency of a microwave, most of the magnetic field generated by a microwave antenna which is provided around the diamond crystal is transmitted and applied onto NV centers in a diamond crystal.

This makes it possible to attain a highly-sensitive magnetometer without providing a plurality of photodiodes in respective orientations and without necessitating an optical component such as a dichroic mirror which separates excitation light and fluorescence from each other.

In a thickness direction of the diamond sensor, the diamond sensor case and the photodiode are located close to each other with the lens interposed therebetween, by which the small thickness can be achieved. Also, in terms of an area, only the microwave coil is provided outside the diamond sensor case.

Therefore, an effective area in the diamond sensor can be increased. By providing the reflection film on a surface which does not come into contact with the excitation light source and the lenses, it is possible to enhance excitation efficiency and fluorescence collection efficiency, and it is also possible to keep a module structurally small.

Hereinafter, embodiments will be described in detail.

First Embodiment

<Structure of Magnetometer>

Figure 2:
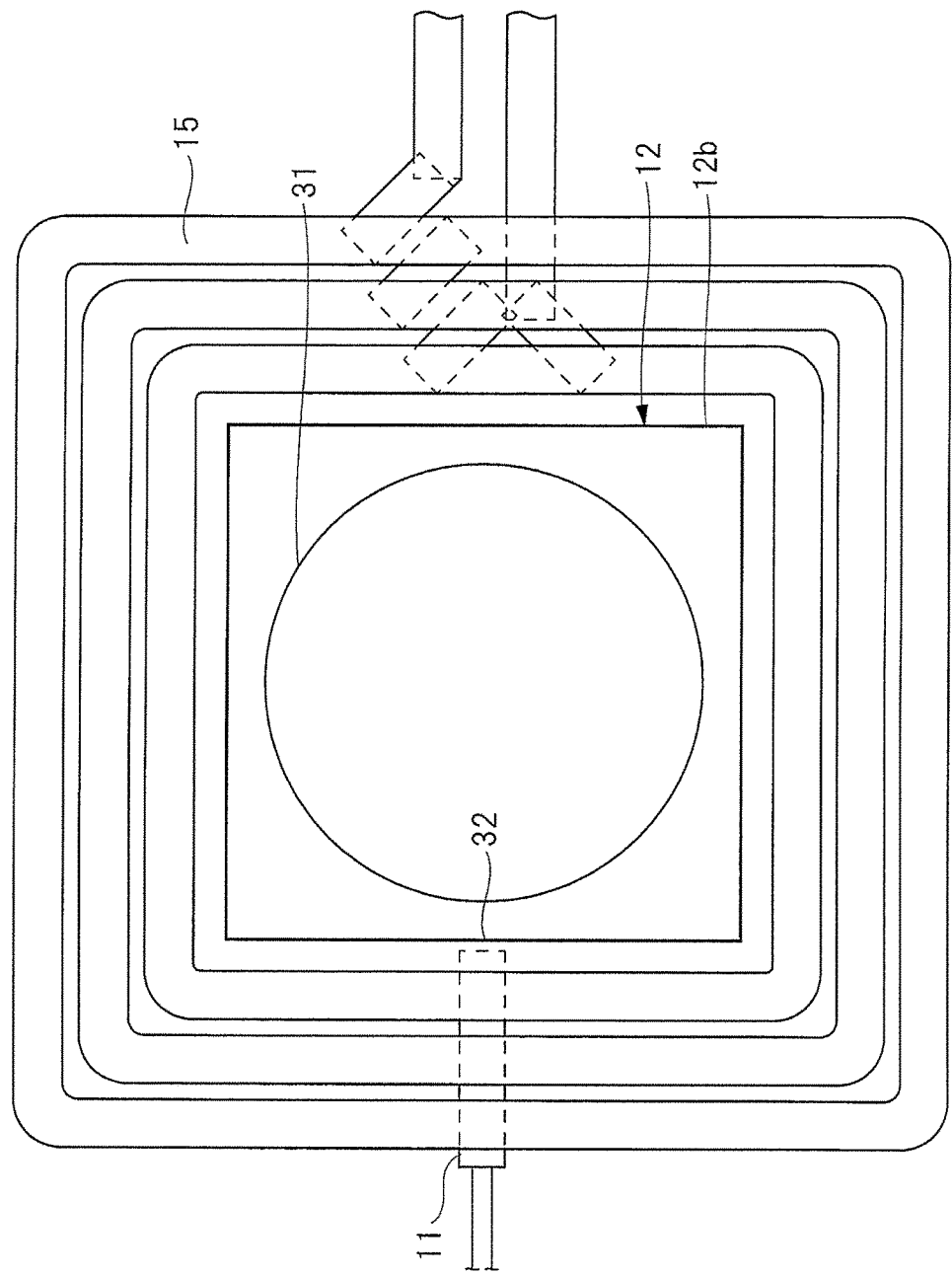
FIG. 2 is a plan view of a diamond sensor unit and a microwave coil included in the magnetometer shown in FIG. 1.

FIG. 1 is an explanatory drawing showing an example of a structure of a magnetometer according to a first embodiment. FIG. 2 is a plan view of a diamond sensor unit and a microwave coil included in the magnetometer shown in FIG. 1.

A magnetometer 10 has a module package structure, and the magnetometer 10 is made thinner and smaller. As shown in FIG. 1 and FIG. 2, the magnetometer 10 includes an excitation light source 11, a diamond sensor unit 12, a low-pass filter 13, a photodiode 14, a microwave coil 15, lenses 16 and 17, a signal processing circuit 18, a microwave circuit 19, and a control circuit 20.

The lens 16 which is a first lens is provided on the diamond sensor unit 12. More specifically, the lens 16 is provided on a fluorescence output window 31 formed in a diamond sensor case 12b described later.

The low-pass filter 13 is provided above the lens 16 at a certain distance from the lens 16. The photodiode 14 which is a fluorescence intensity detecting unit is provided above the low-pass filter 13 at a certain distance from the low-pass filter 13. The lens 17 which is a second lens is provided on a light receiving surface of the photodiode 14, in other words, a surface of the photodiode 14 on a side closer to the low-pass filter.

The excitation light source 11 is provided in the vicinity of one side surface of the diamond sensor unit 12. Also, the microwave coil 15 is wound in the peripheral portion of the diamond sensor unit 12 by the predetermined number of turns.

The signal processing circuit 18, the microwave circuit 19, and the control circuit 20 are provided above the photodiode 14. Each of the signal processing circuit 18, the microwave circuit 19, and the control circuit 20 is formed of an individual semiconductor chip.

The signal processing circuit 18, the microwave circuit 19, and the control circuit 20 are mounted onto, for example, a package board (not shown) by solder bumps (not shown) or the like. The package board is provided on a side where a surface opposite to the light receiving surface of the photodiode 14 is provided, for example.

The signal processing circuit 18, the microwave circuit 19, and the control circuit 20 are connected with each other by wiring patterns or the like formed in the package board, for example. Also, the signal processing circuit 18 and the photodiode 14, the control circuit 20 and the excitation light source 11, and the microwave circuit 19 and the microwave coil 15 are connected with each other by, for example, bonding wires (not shown), respectively. These are insulated from each other by, for example, an insulating film (not shown) which is made of silicon dioxide ($SiO_2$) or the like.

Then, the excitation light source 11, the diamond sensor unit 12, the low-pass filter 13, the photodiode 14, the microwave coil 15, the lenses 16 and 17, the signal processing circuit 18, the microwave circuit 19, and the control circuit 20 are sealed with a thermosetting resin, for example, so that a rectangular package (not shown) is formed.

In addition, though FIG. 1 shows an example in which the signal processing circuit 18, the microwave circuit 19, and the control circuit 20 are each formed of different semiconductor chips, those circuits may be formed of one semiconductor chip or two semiconductor chips.

The diamond sensor unit 12 includes, for example, a diamond sensor 12a having a shape of a quadrilateral plate and a diamond sensor case 12b having a shape of a case, with which the diamond sensor 12a is covered.

In the diamond sensor case 12b, the fluorescence output window 31 which is a first window and an excitation-light reception window 32 which is a second window are formed. The fluorescence output window 31 is a window through which fluorescence generated by the diamond sensor 12a is output.

The fluorescence output window 31 has a circular shape, for example, and is formed on a back surface side opposite to a magnetism measurement surface, which is a main surface of the diamond sensor 12a, in the diamond sensor case 12b. The magnetism measurement surface is a first surface, and a back surface is a second surface.

The excitation-light reception window 32 is a window through which excitation light emitted from the excitation light source 11 is received, and has a circular shape like the fluorescence output window 31, for example. The excitation-light reception window 32 is formed in a side surface of the diamond sensor case 12b, where the above-descried excitation light source 11 is provided.

In other words, the excitation-light reception window 32 is formed in a side surface where the excitation light source 11 is provided, out of four side surfaces which are orthogonal to the magnetism measurement surface as the first surface and the back surface as the second surface, respectively.

In addition, though FIG. 1 shows an example in which the excitation-light reception window 32 is formed in a certain side surface, the number of excitation-light reception windows 32 is not limited to any specific number, and two or more excitation-light reception windows 32 may be formed in each of side surfaces, for example.

Also, though FIG. 1 shows an example in which each of the fluorescence output window 31 and the excitation-light reception window 32 has a circular shape, the shape of each of the fluorescence output window 31 and the excitation-light reception window 32 is not limited to any specific shape.

The reflection film 30 is formed on either a front surface or an inner surface of the diamond sensor case 12b, except portions where the fluorescence output window 31 and the excitation-light reception window 32 are formed. In this regard, FIG. 1 shows an example in which the reflection film 30 is formed on the inner surface of the diamond sensor case 12b.

Namely, the fluorescence output window 31 and the excitation-light reception window 32 are regions where the reflection film 30 is not formed on either the front surface or the inner surface of the diamond sensor case 12b. The reflection film 30 is a metal film, and is made of, for example, titanium, copper, aluminum, or the like.

The diamond sensor 12a includes numerous nitrogen-vacancy centers, i.e., NV centers, and emits fluorescence when being irradiated with excitation light by the excitation light source 11. Then, intensity of a magnetic field is detected by utilizing the fact that dependence of fluorescence intensity upon a frequency of a microwave applied by the microwave coil 15 at that time depends sharply on the magnetic field. Detection sensitivity of the magnetic field depends on fluorescence collection efficiency.

The microwave coil 15 applies a microwave onto the diamond sensor unit 12. A magnetic field generated by the microwave coil 15 is set so as to be perpendicular to the main surface of the diamond sensor 12a.

The excitation light source 11 irradiates the diamond sensor 12a with excitation light. The photodiode 14 detects intensity of fluorescence generated from the diamond sensor case 12b. The signal processing circuit 18 detects intensity of the fluorescence captured by the photodiode 14. The control circuit 20 controls operations of the excitation light source 11, the microwave circuit 19, and the signal processing circuit 18.

Excitation light which is emitted by the excitation light source 11 and received by the diamond sensor 12a through the excitation-light reception window 32 is multi-reflected by the reflection film 30 formed in the diamond sensor case 12b, and is confined in the diamond sensor case 12b. Though a part of the excitation light is output via the lens 16, it is reflected by the low-pass filter 13 described later and is returned to the diamond sensor 12a.

On the other hand, since the diamond sensor 12a includes numerous nitrogen-vacancy centers as described above, the fluorescence output from the NV centers which are irradiated with excitation light is also multi-reflected and confined inside the diamond sensor 12a. A part thereof is output to the photodiode 14 via the lens 16 and the low-pass filter 13.

Since excitation light and fluorescence are multi-reflected by the reflection film 30 within the diamond sensor case 12b as described above, even the single photodiode 14 alone can sufficiently collect the fluorescence.

The excitation light source 11 is formed of, for example, a semiconductor laser or a light emitting diode (LED), and outputs excitation light with a wavelength of, for example, about 533 nm or shorter. Operations for light emission in the excitation light source 11 are controlled by the control circuit 20.

The microwave circuit 19 supplies a microwave having controlled amplitude and a controlled frequency to the microwave coil 15. The amplitude and frequency of the microwave are controlled by the control circuit 20.

A relationship of f=|B0*28.07−2.87| [GHz] needs to be satisfied between a frequency f [GHz] of a microwave and a static magnetic field B0 [unit: T (tesla)] applied onto the diamond sensor 12a. In the above formula, | | represents an absolute value.

The diamond sensor 12a is either a single crystal synthesized by a high pressure-high temperature (HPHT) method, or a polycrystalline thin film formed by a chemical vapor deposition (CVD) process which is one of vapor deposition processes on a single crystal synthesized by the HPHT method. Alternatively, the diamond sensor 12a is a polycrystalline thin film which is formed by the CVD process on a substrate of a different material such as a molybdenum substrate or a silicon substrate through heteroepitaxial growth. A polycrystalline thin film is advantageous over a single-crystalline thin plate in that it can be manufactured at a lower cost.

The low-pass filter 13 has a structure in which a dielectric thin film is stacked on a glass surface, for example. Herein, total reflection occurs under a condition of t=λ/2/n/tan α where a refractive index and a thickness of the dielectric thin film are "n" and "t", a wavelength of excitation light is "λ", and an incident angle of excitation light to the low-pass filter 13 is α.

Since excitation light is monochromic light, λ is constant. As a dielectric, for example, titanium oxide ($TiO_2$), aluminum oxide ($Al_2O_3$), or the like which has high mechanical strength and a high refractive index is preferable.

A fluorescence signal captured by the photodiode 14 is output to the signal processing circuit 18. The signal processing circuit 18 carries out operations such as signal integration and background noise subtraction a predetermined number of times. The control circuit 20 includes, for example, a microcontroller and the like. The control circuit 20 controls the excitation light source 11, the signal processing circuit 18, and the microwave circuit 19 by supplying timing signals thereto.

<Example of Structure of Diamond Sensor Unit>

Next, a structure of the diamond sensor unit 12 will be described in detail with reference to FIG. 3.

Figure 3:
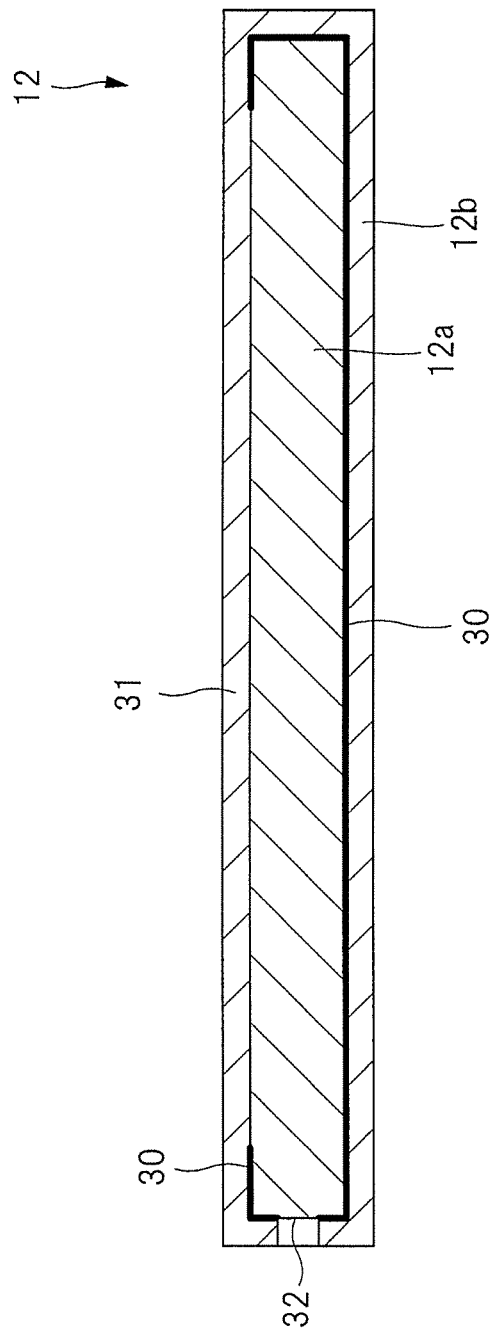
FIG. 3 is an explanatory drawing showing an example of across section of the diamond sensor unit included in the magnetometer shown in FIG. 1.

FIG. 3 is an explanatory drawing showing an example of a cross section of the diamond sensor unit 12 included in the magnetometer 10 shown in FIG. 1. FIG. 3 shows an example in which the reflection film 30 is formed on the inner surface of the diamond sensor case 12b.

As described above, the diamond sensor case 12b has a shape of a case with which the diamond sensor 12a having a plate shape is covered, for example. The reflection film 30 is formed on the inner surface of the diamond sensor case 12b except portions where the fluorescence output window 31 and the excitation-light reception window 32 are formed.

The diamond sensor case 12b is made of, for example, an insulating structural material such as ceramic, glass, or plastic. Also, the fluorescence output window 31 and the excitation-light reception window 32 are regions where the reflection film 30 is not formed.

Since a transparent material such as glass transmits excitation light, regions where the reflection film 30 is not formed serve as the fluorescence output window 31 and the excitation-light reception window 32. FIG. 3 shows an example in which the diamond sensor case 12b is made of a transparent material.

On the other hand, in a case where the diamond sensor case 12b is made of a non-transparent material such as ceramic, the diamond sensor case 12b does not transmit excitation light. Thus, regions for the fluorescence output window 31 and the excitation-light reception window 32 are cut out, thereby forming these windows.

The reflection film 30 is, for example, a metal film and has a thickness which is smaller than a skin-effect depth at a frequency of a microwave and is larger than a skin-effect depth at a frequency of light. Accordingly, the reflection film 30 reflects most of light and transmits most of microwave.

Consequently, a magnetic field generated by the microwave coil 15 provided in the peripheral portion of the diamond sensor case 12b is mostly transmitted, and is applied onto NV centers in the diamond sensor 12a. As a result, it is possible to attain the magnetometer 10 with a miniaturized structure while enhancing fluorescence collection efficiency.

Also, the diamond sensor case 12b may be obtained by forming the reflection film 30 on a thin vinyl or the like. In such a case, the diamond sensor case 12b is formed by sticking a vinyl, on which the reflection film 30 is formed, to the diamond sensor 12*a*. In this manner, the diamond sensor unit 12 can be easily formed.

<Thickness of Reflection Film>

Figure 4:
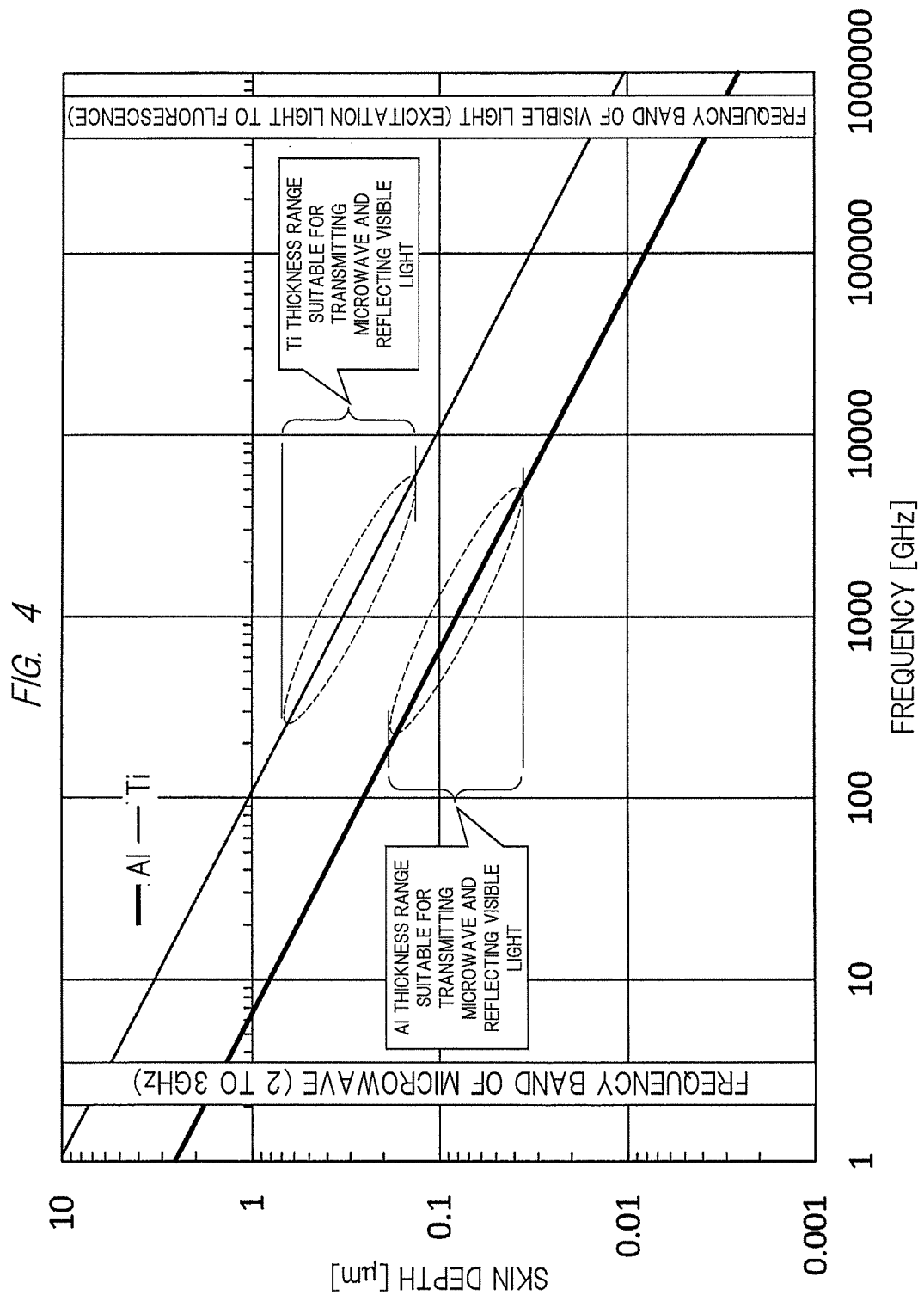
FIG. 4 is an explanatory drawing showing an example of a frequency dependence of an AC current skin depth of titanium and aluminum which are used as materials forming a reflection film in FIG. 3.

FIG. 4 is an explanatory drawing showing an example of a frequency dependence of an AC current skin depth of titanium and aluminum which are used as materials forming the reflection film 30 in FIG. 3. Note that a skin depth means a depth at which a current density becomes equal to 1/e ("e" represents a bottom of an exponential function) of that in a front surface and is known as $\sqrt{(2\rho/\omega\mu)}$ under the phenomenon in which a current density is highest in the front surface and gradually decreases in depth direction when an AC current flows in a conductor.

In this regard, "$\rho$" represents electrical resistivity of a conductor, "$\omega$" represents an angular frequency of a current (=$2\pi\times$frequency), and "$\mu$" represents absolute magnetic permeability of a conductor.

A frequency dependence of an AC current skin depth of each of titanium and aluminum according to the present formula is as shown in FIG. 4. In FIG. 4, a microwave frequency range of 2 GHz to 3 GHz and a visible-light frequency range of 4 to $8\times10^5$ GHz are shown in an overlapping manner. Also, in FIG. 4, a thick solid line shows a frequency dependence in aluminum (Al), and a thin solid line shows a frequency dependence in titanium (Ti).

It can be considered that a thickness range suitable for transmitting a microwave and reflecting visible light is a skin depth at a frequency of about 1000 GHz which is an intermediate frequency on a logarithmic axis between respective frequencies of a microwave and visible light.

Thus, FIG. 4 indicates that the thickness of the reflection film 30 is preferably about 300 nm for titanium and about 100 nm for aluminum.

<Principles of Measurement of Static Magnetic Field by Magnetometer>

Figure 5:
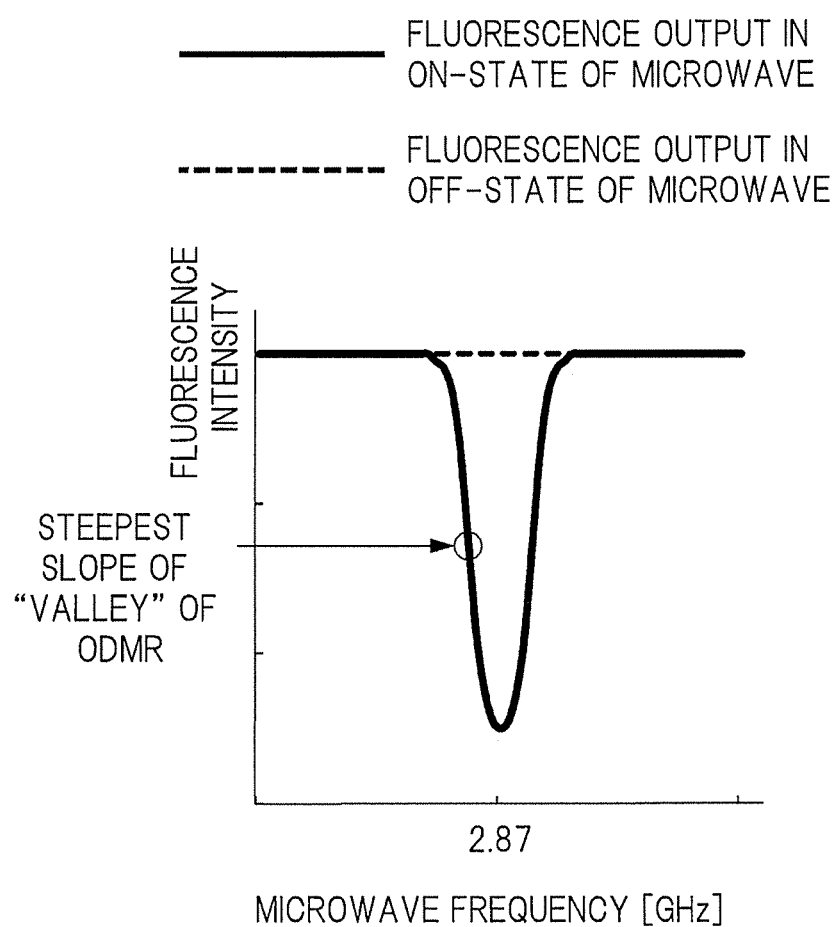
FIG. 5 is an explanatory drawing showing an example of an operation point on ODMR used in measurement of a static magnetic field.

FIG. 5 is an explanatory drawing showing an example of an operation point on ODMR used in measurement of a static magnetic field.

Hereinafter, principles of measurement of a static magnetic field, that is, a DC magnetic field in the magnetometer 10 shown in FIG. 1 will be described with the use of optically detected magnetic resonance (ODMR) of a diamond sensor shown in FIG. 5.

In FIG. 5, a vertical axis represents fluorescence intensity of a diamond sensor, and a horizontal axis represents a frequency of a microwave applied to the diamond sensor. Variation in fluorescence intensity depending on a microwave frequency is referred to as an optically detected magnetic resonance.

In a state where no static magnetic field is applied, a "valley" in fluorescence intensity is located in the vicinity of 2.87 GHz. However, as application of a static magnetic field B0 [unit: tesla] proceeds, a position f of the "valley" on the frequency axis varies while maintaining a relationship of Formula 1 below.

$$f=|B0*28.07-2.87|[GHz] \quad \text{(Formula 1)}$$

At that time, with half a depth of the "valley" of fluorescence intensity being set as a reference value, feedback is carried out using an integral of a difference between an actually-measured value of fluorescence intensity and the above-stated reference value, as a variation amount of the microwave frequency. This allows an operation point to always follow half a depth of the "valley". In this case, magnetic-field variation $\Delta B0$ can be obtained as a value proportional to frequency variation $\Delta f$ by $\Delta B0=\Delta f/28.07$.

Strictly speaking, B which represents a vector quantity is a component of a magnetic field in an orientation of NV centers within the diamond sensor. In a case where there is an orientation distribution of NV centers along respective crystal axes in the diamond sensor, B is a component of a magnetic field in an average orientation which is obtained as a result of weighting using existence ratios of NV centers in respective orientations.

Besides, actually, in order to remove a noise from subtle variation in fluorescence, a microwave is repeatedly turned on/off in a constant cycle. Thus, a vertical axis of ODMR represents a difference in fluorescence intensity between an off-state and an on-state of the microwave.

Also, instead of half a depth of the "valley", a point at the steepest slope in the "valley" can be set as the operation point. In this case, since variation in fluorescence intensity due to variation in magnetic field is largest, the highest sensitivity can be obtained.

Variation in ODMR which occurs at such an operation point when a nuclear magnetization signal as an AC signal reaches the diamond sensor is shown in FIG. 5. A difference in fluorescence intensity is caused between a state in which a nuclear magnetization signal is in a positive phase and a state in which a nuclear magnetization signal is in a negative phase. By measuring the above-stated difference in fluorescence intensity, it is possible to measure intensity of the nuclear magnetization signal. The operation point is placed at the steepest slope in the "valley" in FIG. 5.

<Principles of Measurement of Nuclear Magnetization Signal by Magnetometer>

Also, measurement using the magnetometer 10 in FIG. 1 includes measurement of a nuclear magnetization signal excited by a magnetic field, in other words, measurement of an AC magnetic field in addition to measurement of a static magnetic field (DC magnetic field) for measuring a magnetic sample having spontaneous magnetization or measuring an environmental magnetic field. For the measurement of a nuclear magnetization signal, a static magnetic field and a high-frequency pulse signal with a specific frequency are applied onto a sample, and a high-frequency signal (AC magnetic field), which is induced and emitted after the high-frequency pulse signal is removed, is detected.

In the measurement of a nuclear magnetization signal, a high-frequency signal of absorption/emission of a proton in an atomic nucleus is used. In this case, it is known that the static magnetic field B0 and the high-frequency signal frequency f are in a relationship in which f/B0 has a constant value.

Since a proton is contained in water and an organism usually contains water, a chemical state such as a distribution of water, a solute or a concentration in an organism and a physical state such as a temperature can be detected by the measurement of a nuclear magnetization signal.

In this case, since only a portion of a sample in which f/B0 becomes equal to the above-stated constant value resonates, a state within the sample can be detected with an external magnetometer by adjusting a distribution of a magnetic field. The state within the sample includes a temperature. This is because movement of a molecule varies depending on a temperature and variation in the movement appears in a relaxation time or the like in a nuclear magnetization signal.

In order to carry out measurement of an inside of a sample with a nuclear magnetization signal, the nuclear magnetization signal provided from a measured portion of the sample needs to be effectively detected by a magnetometer at a distant place. Therefore, the magnetometer 10 needs to have a large measureable area.

In this regard, the large measurable area means that a sensor portion capable of detecting a magnetic signal, that is, the diamond sensor 12a has a large area. Also, if the diamond sensor 12a has a large area, it is preferable that the magnetometer has a thin structure for ease of handling. Thus, the magnetometer 10 shown in FIG. 1 is most suitable because it does not use an optical component such as a dichroic mirror and includes only one photodiode.

As described above, the magnetometer 10 which has high fluorescence collection efficiency and is miniaturized can be attained.

Second Embodiment

<Overview>
In the structure according to the first embodiment described above, excitation light is incident from a side surface of the diamond sensor case 12b. Meanwhile, a technique for allowing excitation light to be incident obliquely from above the diamond sensor case 12b will be described in the second embodiment.

Figure 6:
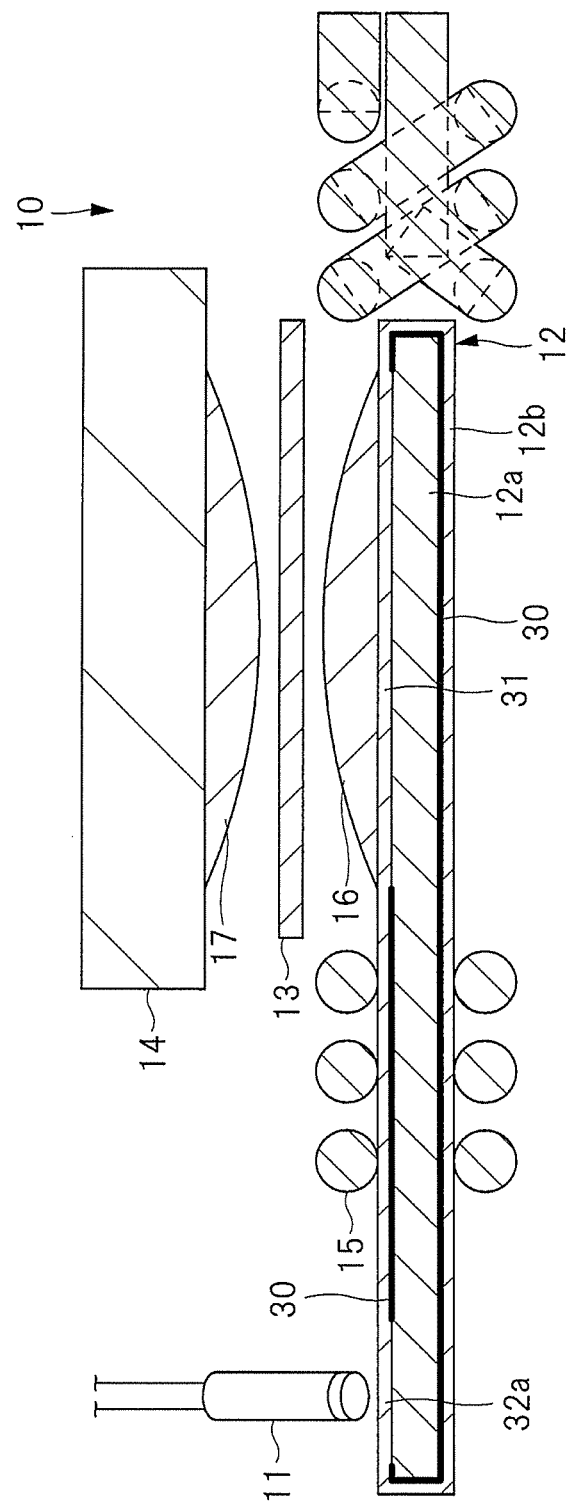
FIG. 6 is an explanatory drawing showing an example of a cross section in a magnetometer according to a second embodiment.
Figure 7:
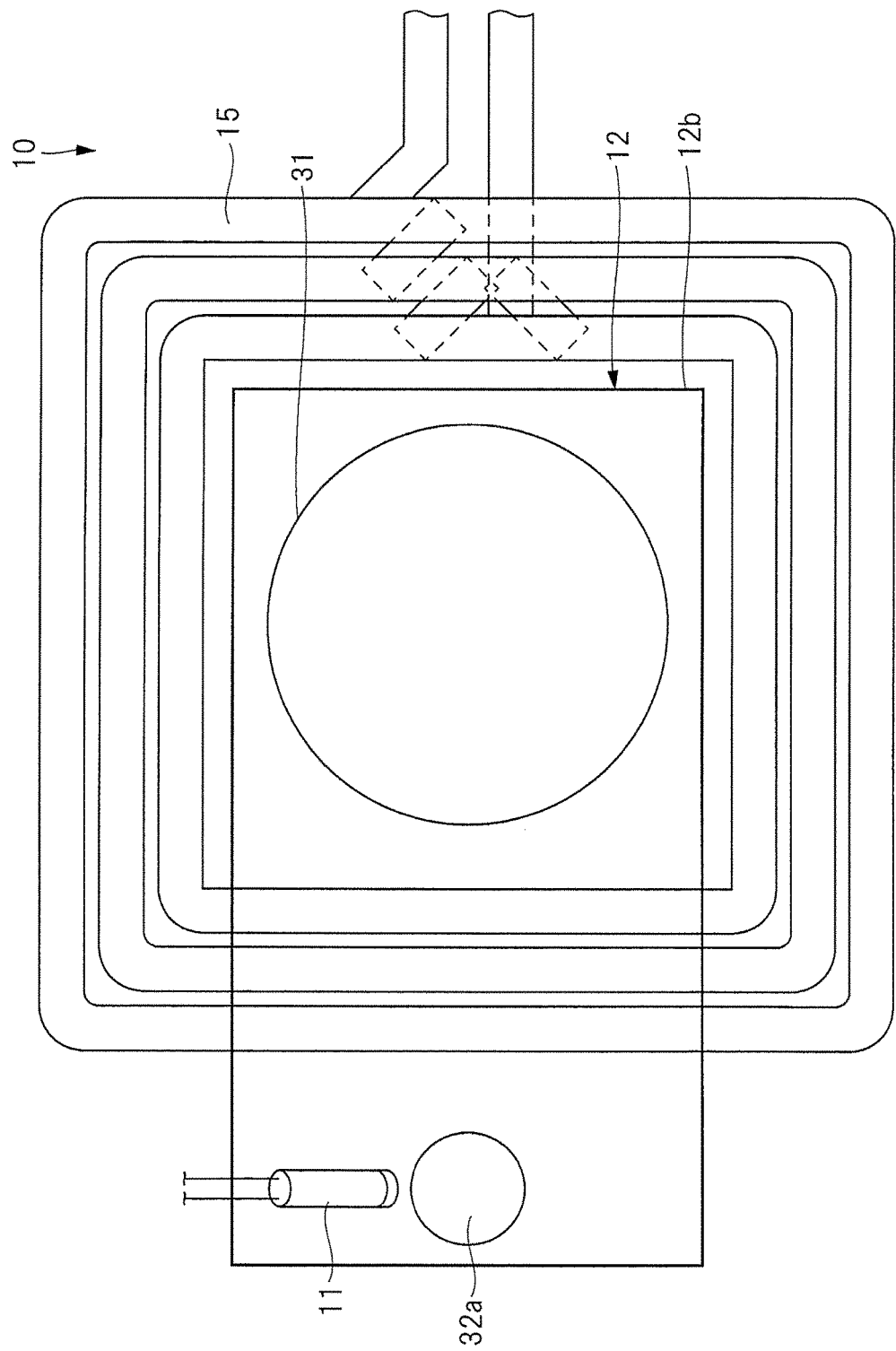
FIG. 7 is a plan view of FIG. 6.

<Example of Structure of Magnetometer>
FIG. 6 is an explanatory drawing showing an example of across section of the magnetometer 10 according to the second embodiment. FIG. 7 is a plan view of FIG. 6. Note that the signal processing circuit 18, the microwave circuit 19, and the control circuit 20 are omitted for simplification in FIG. 6 and FIG. 7.

A difference between the magnetometer 10 shown in FIG. 6 and the magnetometer 10 in FIG. 1 according to the first embodiment described above lies in that excitation light from the excitation light source 11 is not incident on a side surface of the diamond sensor case 12b, but incident obliquely from above a back surface of the diamond sensor case 12b, which is opposite to the magnetism measurement surface of the diamond sensor 12a, as described above.

The diamond sensor 12a included in the diamond sensor unit 12 is formed of a rectangular plate as shown in FIG. 6 and FIG. 7. Thus, the diamond sensor case 12b, with which the diamond sensor 12a is covered, also has a rectangular shape. The excitation light source 11 is provided above a portion in the vicinity of one of shorter sides of the diamond sensor unit 12, in other words, is provided obliquely upward relative to a back surface side of the diamond sensor 12a at a depression angle.

The diamond sensor case 12b having a rectangular shape is a case with which the diamond sensor 12a also having a rectangular shape is covered, and includes the fluorescence output window 31 and an excitation-light reception window 32a.

The fluorescence output window 31 is a window through which fluorescence generated by the diamond sensor 12a is output, and is formed on a back surface side of the diamond sensor 12a. The excitation-light reception window 32a is formed in the vicinity of the one shorter side of the diamond sensor unit 12, above which the excitation light source 11 is provided, so as to receive excitation light from the excitation light source 11 provided above at a depression angle.

Like the case of FIG. 1, each of the fluorescence output window 31 and the excitation-light reception window 32a has a circular shape, but a shape of each of the fluorescence output window 31 and the excitation-light reception window 32a is not limited to any specific shape.

The reflection film 30 is formed on either a front surface or an inner surface of the diamond sensor case 12b, except portions where the fluorescence output window 31 and the excitation-light reception window 32a are formed. Namely, the fluorescence output window 31 and the excitation-light reception window 32a are regions where the reflection film 30 is not formed on either the front surface or the inner surface of the diamond sensor case 12b.

Note that FIG. 6 shows an example in which the reflection film 30 is formed on the inner surface of the diamond sensor case 12b.

Also, the microwave coil 15 is wound by the predetermined number of turns so as to have a square shape in the peripheral portion of the diamond sensor unit 12. In this case, since the diamond sensor unit 12 has a rectangular shape as described above, the microwave coil 15 in the vicinity of one shorter side above which the excitation light source 11 is provided is provided between the excitation light source 11 and the lens 16 so as to be orthogonal to longer sides of the diamond sensor unit 12 instead of in the peripheral portion of the diamond sensor unit 12. The other structure is similar to that in FIG. 1 and FIG. 2 according to the above-described first embodiment, and thus description thereof is omitted.

<Example of Operation of Magnetometer>
An inside of the diamond sensor case 12b is irradiated with excitation light emitted from the excitation light source 11 through the excitation-light reception window 32a of the diamond sensor case 12b. Fluorescence output provided by the diamond sensor unit 12 is multi-reflected by the reflection film 30 in the diamond sensor case 12b, and is then transmitted through the fluorescence output window 31, the lens 16, and the low-pass filter 13, to be incident upon the photodiode 14 through the lens 17. At that time, excitation light is reflected by the low-pass filter 13, and thus does not reach the photodiode 14.

In a case where excitation light is incident from the side surface of the diamond sensor case 12b as in the magnetometer 10 shown in FIG. 1, the beam direction of excitation light and the side surface of the diamond sensor case need to be precisely aligned with each other. For this reason, it is sometimes difficult to reduce the thickness of the diamond sensor case 12b.

On the other hand, in a case where excitation light is incident obliquely from above the diamond sensor case 12b as shown in FIG. 6 and FIG. 7, it is only required to form the excitation-light reception window 32a at a position to which the excitation light is applied in the diamond sensor case 12b. Accordingly, no difficulty in alignment is caused even if the thickness of the diamond sensor case 12b is reduced.

As described above, by allowing excitation light to be incident obliquely from above the diamond sensor case 12b, it is possible to make the diamond sensor unit 12 thinner. Also, a polycrystalline diamond sensor which is manufactured by an integration process and is thus inexpensive compared to a diamond sensor of a mono-crystalline plate which is manufactured by an HPHT method or the like can be manufactured at a particularly lower cost in a case where a thickness thereof is small compared to a case where a thickness thereof is large. Therefore, a cost for the diamond sensor can be reduced by using the present embodiment.

As described above, the magnetometer 10 having a large surface area can be attained at a low cost.

Third Embodiment

<Overview>
The magnetometer 10 according to the first embodiment described above has a structure in which one lens is provided for one diamond sensor unit 12. Meanwhile, a case in which a plurality of lenses are provided for one diamond sensor unit 12 will be described in the third embodiment.

<Example of Structure of Magnetometer>

Figure 8:
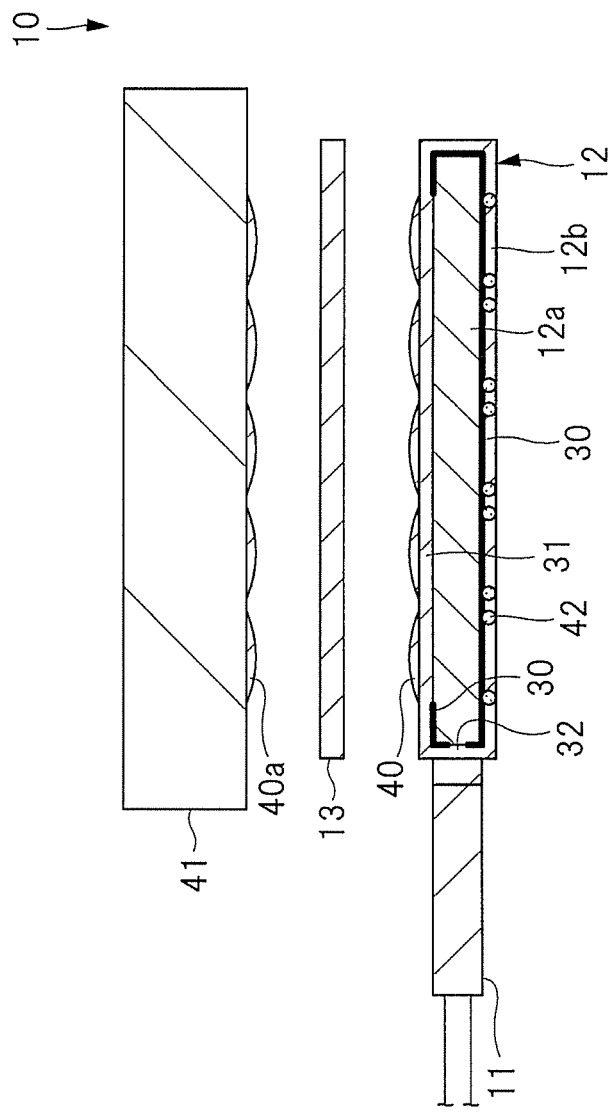
FIG. 8 is an explanatory drawing showing an example of a cross section in a magnetometer according to a third embodiment.
Figure 9:
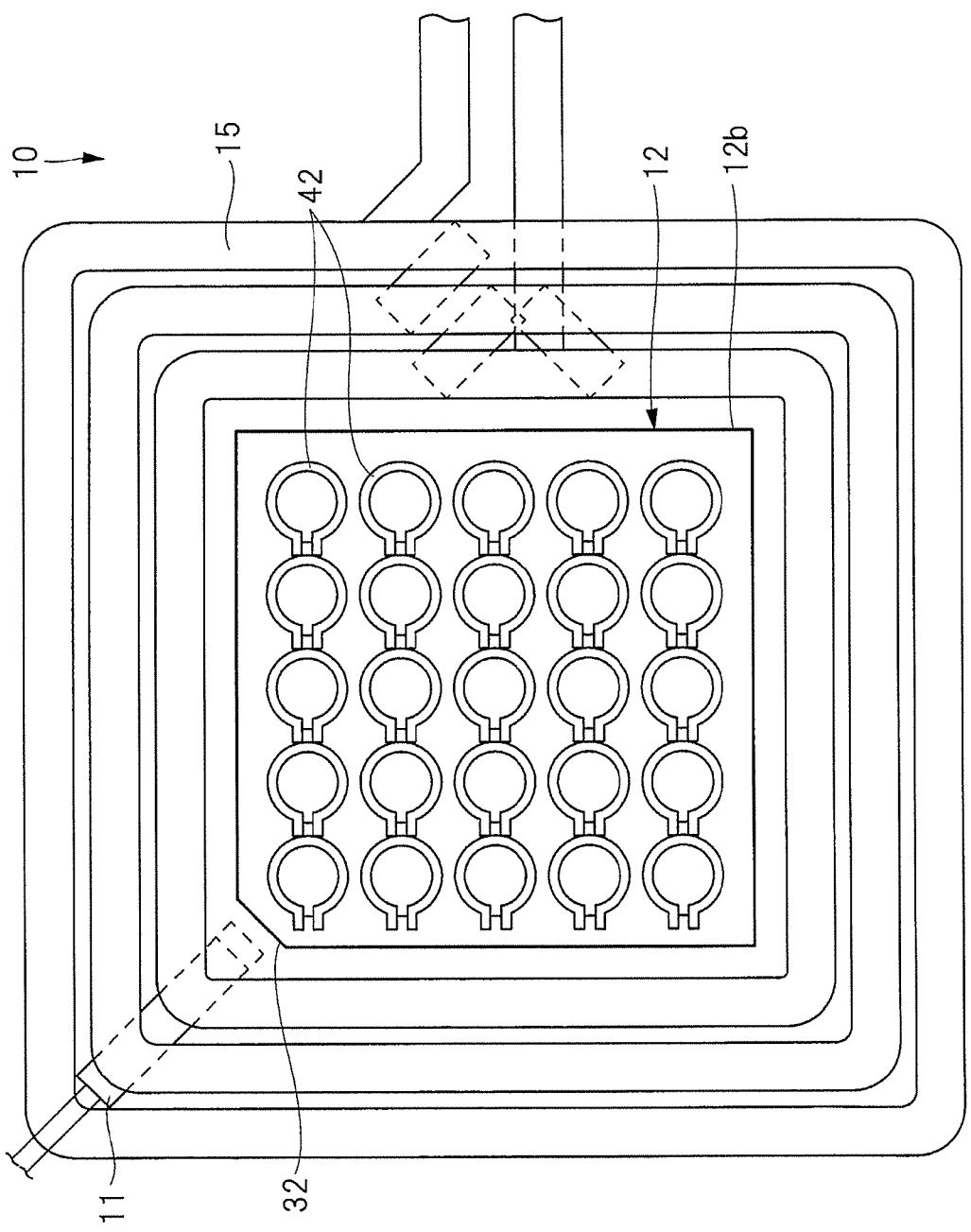
FIG. 9 is a plan view of FIG. 8.

FIG. 8 is an explanatory drawing showing an example of a cross section of the magnetometer 10 according to the third embodiment. FIG. 9 is a plan view of FIG. 8. FIG. 9 is a plan view of the magnetometer 10 viewed from a magnetism measurement surface, that is, a main surface of the diamond sensor 12a. Note that the signal processing circuit 18, the microwave circuit 19, and the control circuit 20 are omitted for simplification in FIG. 8 and FIG. 9.

A difference between the magnetometer 10 shown in FIG. 8 and FIG. 9 and the magnetometer 10 in FIG. 1 and FIG. 2 according to the above-described first embodiment lies in that each of the lenses 16 and 17 is not formed of a single lens, but is formed of a plurality of micro lenses 40 and 40a.

Another difference lies in that a light receiving element is not the photodiode 14, but an image sensor 41 serving as a fluorescence intensity detecting unit. The image sensor 41 is formed of, for example, a charge coupled device (CCD), a complementary metal oxide semiconductor (CMOS) sensor, or the like.

Further, a position of the excitation light source 11 is also different, and the excitation light source 11 is provided in the vicinity of a certain one corner of the diamond sensor unit 12. In this case, the excitation-light reception window 32 is formed in the corresponding corner of the diamond sensor unit 12, in the vicinity of which the excitation light source 11 is provided.

As shown in FIG. 9, the excitation-light reception window 32 is formed by, for example, a process of cutting out the corner portion of each of the diamond sensor 12a and the diamond sensor case 12b in FIG. 8. The excitation-light reception window 32 formed of the cut-out corner is irradiated with excitation light by the excitation light source 11.

In addition, though FIG. 9 shows an example in which the excitation-light reception window 32 is formed at one corner portion of each of the diamond sensor 12a and the diamond sensor case 12b, the number of excitation-light reception windows 32 is not limited to any specific number as long as the number of excitation-light reception windows 32 is equal to the number of excitation light sources 11.

The micro lenses 40a are provided in an array form on a light-receiving surface of the image sensor 41, in other words, a surface facing the low-pass filter 13 of the image sensor 41. Each of the micro lenses 40a is provided so as to correspond to one pixel or some pixels included in the image sensor 41.

Also, the micro lenses 40 are provided in the fluorescence output window 31 formed in the diamond sensor case 12b. The micro lenses 40 are the same in number as the micro lenses 40a, and are each provided in an array form at positions facing the micro lenses 40a.

Also, the magnetometer 10 shown in FIG. 8 and FIG. 9 has a structure in which a plurality of micro coils 42 are provided in addition to the microwave coil 15 provided in the peripheral portion of the diamond sensor unit 12. Note that the microwave coil 15 is omitted in FIG. 8.

The micro coils 42 are formed on the magnetism measurement surface which is the main surface of the diamond sensor 12a. Each of the micro coils 42 is formed so as to follow a shape of the micro lens 40.

Each of the micro coils 42 is connected to the microwave circuit 19 shown in FIG. 1, and applies a microwave with a different frequency for each region in the diamond sensor unit 12, that is, each micro lens 40 by the microwave circuit 19. The other structure is similar to that in FIG. 1 and FIG. 2 according to the above-described first embodiment, and thus description thereof is omitted.

<Example of Measurement of Magnetometer>

In the measurement of a static magnetic field (DC magnetic field), the static magnetic field B0 is determined by the (Formula 1) based on the position f of a "valley" of ODMR on a frequency axis, and a whole visual field of the image sensor 41 is measured based on divided regions for each of the plurality of micro lenses 40 according to the present embodiment. Thus, a static magnetic field in each of regions for the micro lenses 40a can be measured. In the measurement of the static magnetic field (DC magnetic field), the static magnetic field B0 is determined by the (Formula 1) based on the position f of the "valley" of ODMR on a frequency axis, and the static magnetic field is measured based on divided regions for each of the plurality of micro lenses 40 according to the present embodiment. Thus, the static magnetic field in each of regions for the micro lenses 40a can be measured.

At that time, it is also possible to measure the "valley" of ODMR for each of the regions by sweeping a frequency of the microwave coil 15 provided so as to surround the diamond sensor unit 12. Also, by irradiating some of the micro coils 42 provided for the respective micro lenses 40 with microwaves having different frequencies at the same time, the time required to measure the position of the "valley" of ODMR on the frequency axis for each of the regions can be shortened.

As described above, also in the measurement of a nuclear magnetization signal (AC magnetic field), the nuclear magnetization signal for each of the micro lenses 40a of the image sensor 41 can be measured. Here, in a case where a difference is present among respective static magnetic fields of each of the micro lenses 40 of the diamond sensor 12a, it is effective to determine the steepest slope of the "valley" for each of the micro lenses 40 for the sensitivity improvement.

By irradiating each of the micro coils 42 provided for the micro lenses 40 with a microwave having a frequency adjusted to the steepest slope of the "valley" for each of the micro lenses 40, sensitivity improvement in measurement of a distribution of nuclear magnetization signals can be achieved.

In addition, though FIG. 8 and FIG. 9 show a structure in which excitation light is emitted by the excitation light source 11 through the corner of the diamond sensor unit 12, the way of emitting excitation light is not limited to this. For example, excitation light may be emitted from a side surface of the diamond sensor unit 12 or may be emitted obliquely from above the diamond sensor unit 12 as shown in FIG. 1 and FIG. 6.

Fourth Embodiment

<Overview>

In a fourth embodiment, the magnetometer 10 which is less likely to be affected by an electromagnetic wave noise will be described.

In the magnetometer 10 according to the above-described third embodiment, the diamond sensor unit 12 and the image sensor 41 are located close to each other, so that the diamond sensor 12a may probably be affected by an electromagnetic wave noise generated by the image sensor 41.

In order to avoid the influence from the electromagnetic wave noise generated by the image sensor 41 like this, the diamond sensor case 12b and the image sensor 41 need to be located apart from each other in some cases.

<Example of Structure of Magnetometer>

Figure 10:
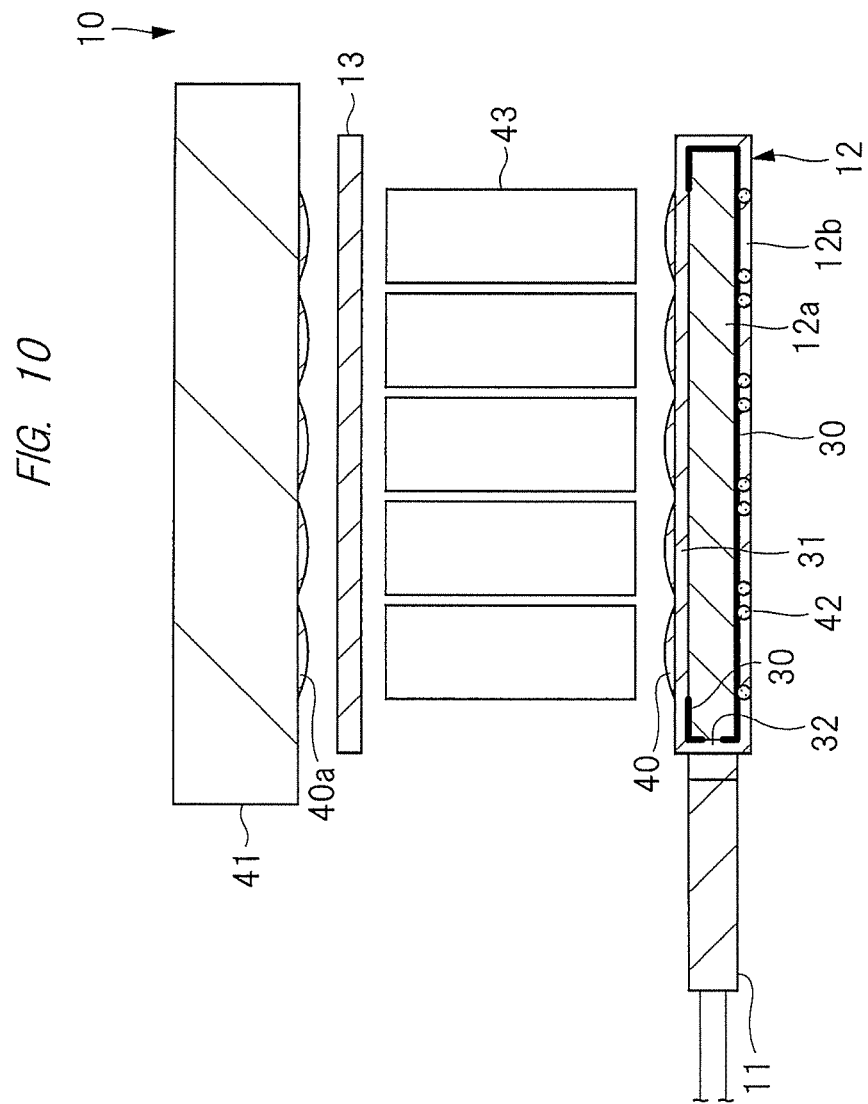
FIG. 10 is an explanatory drawing showing an example of a cross section in a magnetometer according to a fourth embodiment.

FIG. 10 is an explanatory drawing showing an example of a cross section of the magnetometer 10 according to the fourth embodiment.

In the magnetometer 10 shown in FIG. 10, a plurality of optical path guides 43 are provided between the low-pass filter 13 and the diamond sensor unit 12. The other structure is similar to that in FIG. 8 and FIG. 9 according to the above-described third embodiment.

The optical path guides 43 are provided so that the diamond sensor case 12b and the image sensor 41 are kept apart from each other in order to avoid the influence of an electromagnetic wave noise generated by the image sensor 41. The optical path guides 43 are provided so as to correspond to the micro lenses 40, respectively.

The optical path guides 43 are made of, for example, glass and function to suppress scattering of excitation light which is collected by the micro lenses 40. The collected excitation light is reflected in the optical path guides 43, and reaches a side where the micro lenses 40a are provided. Accordingly, excitation light can be efficiently collected while keeping the distance between the diamond sensor unit 12 and the image sensor 41.

In the above-described manner, the magnetometer 10 which is less likely to be affected by an electromagnetic wave noise can be attained without reducing sensitivity in magnetism measurement.

Also in this embodiment, excitation light from the excitation light source 11 may be emitted from a side surface of the diamond sensor unit 12 or may be emitted obliquely from above the diamond sensor unit 12 as shown in FIG. 1 and FIG. 6.

Fifth Embodiment

<Overview>

A technique capable of performing the irradiation of excitation light with higher intensity and a higher degree of uniformity by providing a plurality of excitation light sources 11 will be described in a fifth embodiment.

More specifically, the plurality of excitation light sources 11 are disposed between the diamond sensor unit 12 and the photodiode 14 to irradiate the diamond sensor unit 12 with the excitation light.

<Example of Structure of Magnetometer>

Figure 11:
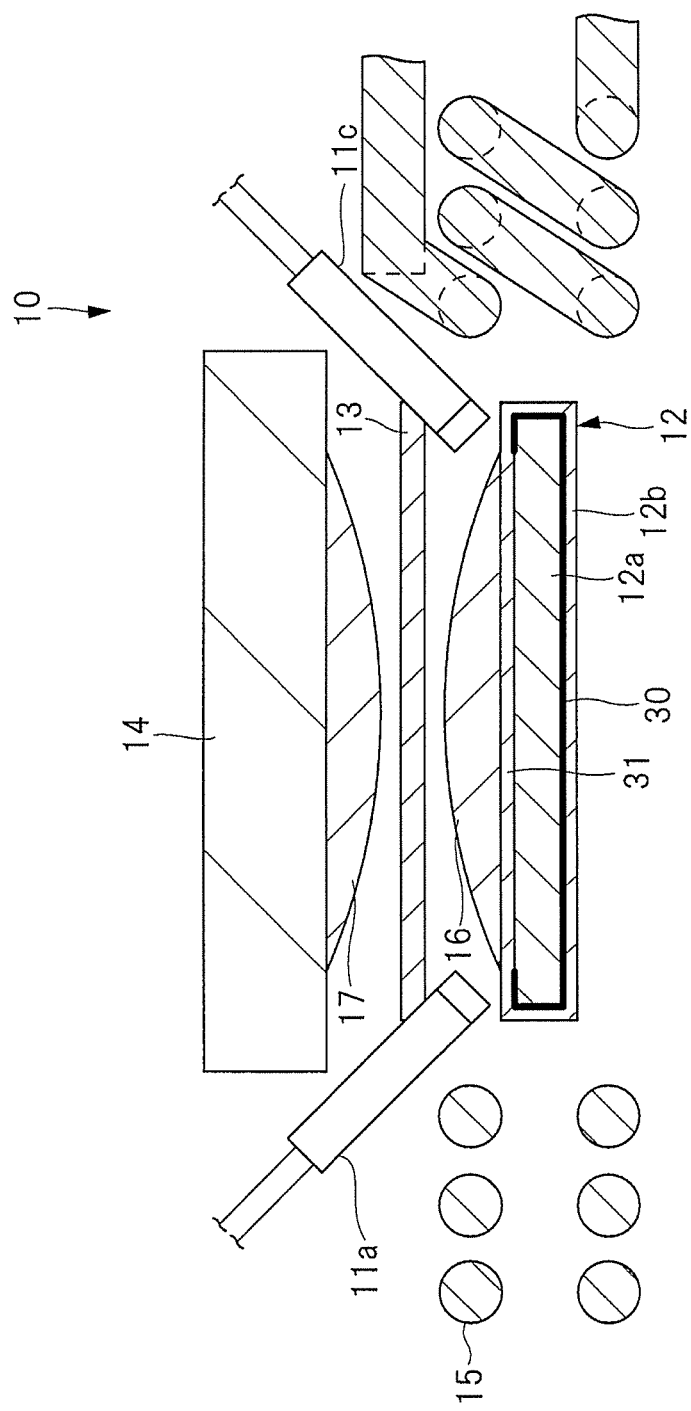
FIG. 11 is an explanatory drawing showing an example of a cross section in a magnetometer according to a fifth embodiment.
Figure 12:
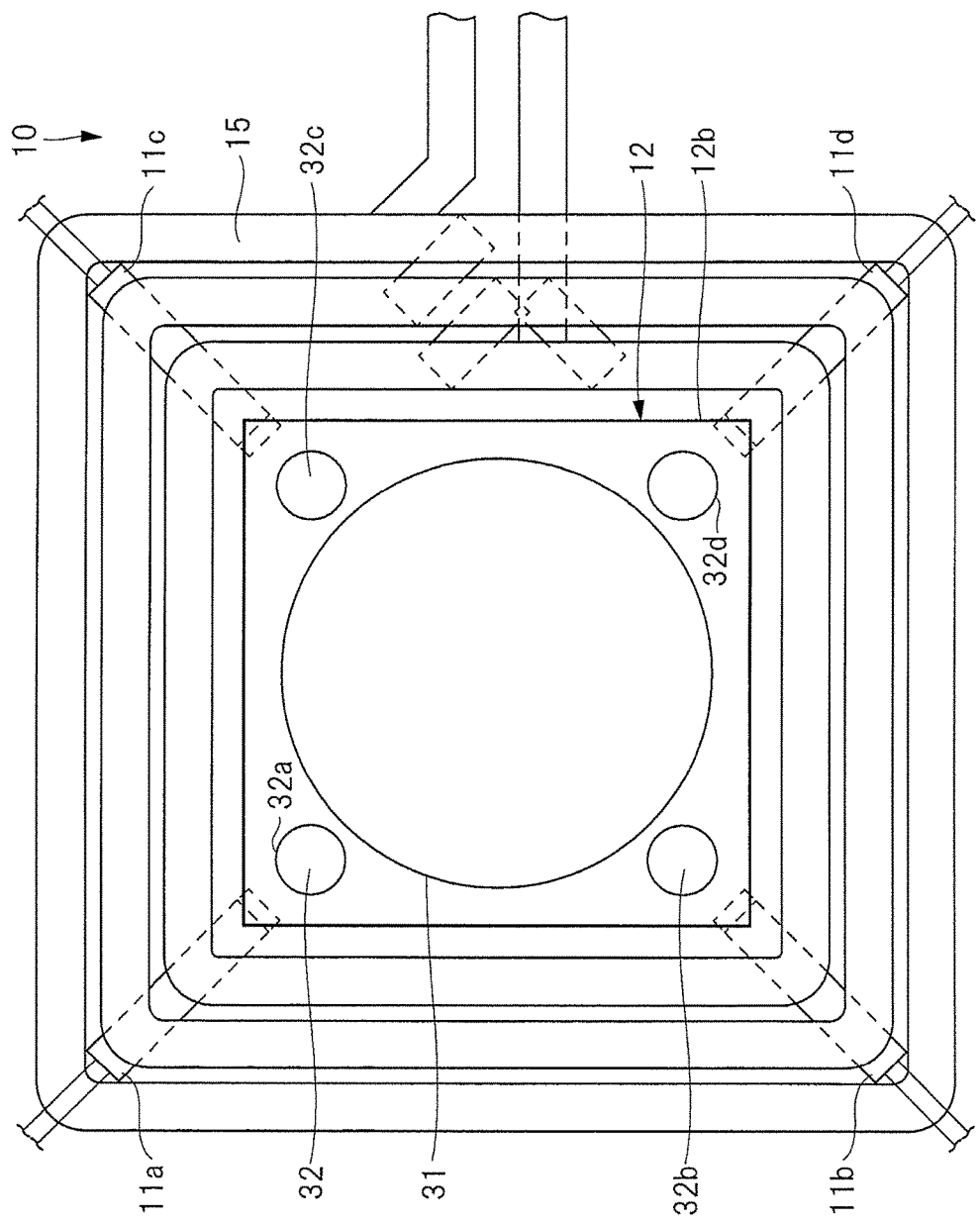
FIG. 12 is a plan view of FIG. 11.

FIG. 11 is an explanatory drawing showing an example of a cross section of the magnetometer 10 according to the fifth embodiment. FIG. 12 is a plan view of FIG. 11.

The magnetometer 10 shown in FIG. 11 and FIG. 12 includes four excitation light sources 11a to 11d. The excitation light sources 11a, 11b, 11c, and 11d are separately provided obliquely upward relative to four corners of the diamond sensor unit 12 at a depression angle.

Also, at the four corners of the diamond sensor case 12b included in the diamond sensor unit 12, excitation-light reception windows 32a to 32d are formed on a back surface side of the diamond sensor 12a. Each of the excitation-light reception windows 32a to 32d has a circular shape, but a shape of each of the excitation-light reception windows 32a to 32d is not limited to this. The other structure is similar to that in FIG. 1 and FIG. 2 according to the above-described first embodiment.

Excitation light emitted from the excitation light sources 11a to 11d gives incident light into the diamond sensor case 12b through the excitation-light reception windows 32a to 32d, respectively. In this manner, incident light can be given from four corners of the diamond sensor case 12b, so that a whole inside of the diamond sensor case 12b can be irradiated with stronger excitation light, and excitation light received by the inside of the diamond sensor case 12b can have intensity with a higher degree of uniformity.

In the above-described manner, intensity of fluorescence generated by the diamond sensor 12a can be further increased, and sensitivity of the magnetometer can be further improved.

<Intentional Distribution of Excitation Light>

Further, it is also possible to intentionally provide a distribution in the intensity of excitation light received by the inside of the diamond sensor case 12b.

Figure 13:
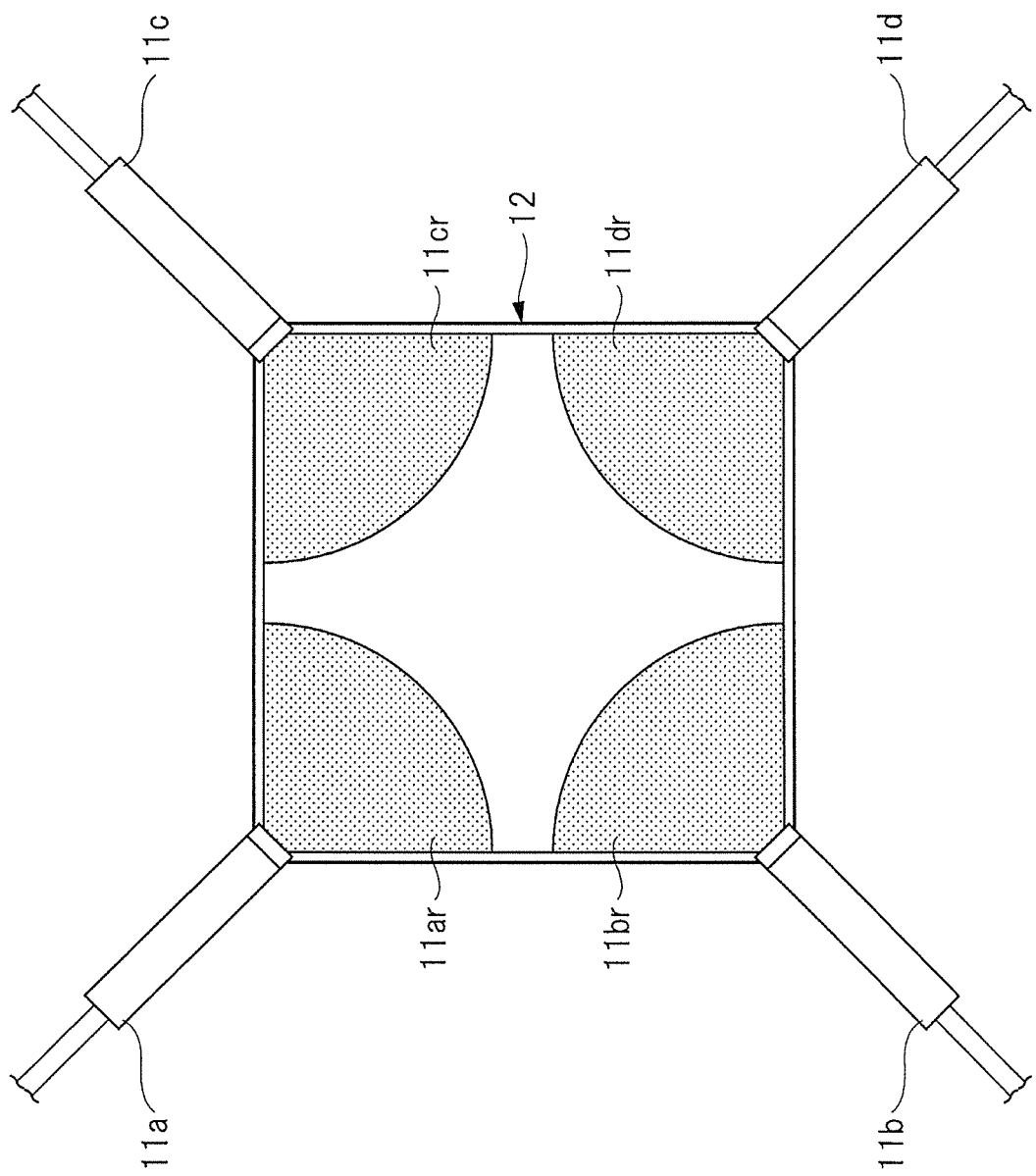
FIG. 13 is an explanatory drawing schematically showing irradiation regions of excitation light sources shown in FIG. 11 and FIG. 12.

FIG. 13 is an explanatory drawing schematically showing irradiation regions of the excitation light sources 11a to 11d shown in FIG. 11 and FIG. 12.

In FIG. 13, an irradiation region 11ar shown by shading indicates a range of excitation light emitted by the excitation light source 11a. Similarly, irradiation regions 11br to 11dr shown by shading indicate ranges of excitation lights emitted by the excitation light sources 11b to 11d, respectively.

Here, the irradiation regions 11ar to 11dr will be described.

Excitation light provided from each of the excitation light sources 11a to 11d is repeatedly multi-reflected within the diamond sensor case 12b, so that the excitation light spreads over the inside of the diamond sensor 12a.

However, it is inevitable that the excitation light is lost to some extent during the reflection by the reflection film 30 in the diamond sensor 12a. Thus, the irradiation regions 11ar to 11dr indicate that portions located close to the excitation light sources 11a to 11d are irradiated most strongly.

For example, when it is desired to measure a magnetic field of the irradiation region 11ar, it is only required to perform the irradiation by the excitation light source 11a. Also, when it is desired to measure a weighted magnetic field of each of the irradiation regions 11ar to 11dr, it is only required to weight the intensity of each of the excitation light sources 11a to 11d correspondingly.

In this manner, it is possible to carry out magnetism measurement in which weighting is carried out for each region in the diamond sensor 12a, while suppressing the overall power consumption for excitation light.

Though this embodiment shows an example in which the four excitation light sources 11a, 11b, 11c, and 11d are provided and excitation light is emitted obliquely from above each of four corners of the diamond sensor unit 12, the irradiation position of the excitation light is not limited to this.

For example, the structure in FIG. 1 according to the above-described first embodiment may be modified so as to use four excitation light sources. In such a case, the four excitation light sources are configured to emit excitation light from the four side surfaces of the diamond sensor unit 12, respectively. As a matter of course, the excitation-light reception window 32a is provided in each of four side surfaces of the diamond sensor case 12b.

Sixth Embodiment

<Overview>

In a sixth embodiment, principles, drive timing, and setting of an operation point in a technique for measuring a nuclear magnetization signal of water to which a magnetometer is applied will described with reference to FIG. 14 to FIG. 16.

<Principles of Method of Measuring Nuclear Magnetization of Water>

First, principles for application of the magnetometer 10 according to the above-described first to fifth embodiments to measurement of a nuclear magnetization signal of water will be described with reference to FIG. 14.

Figure 14:
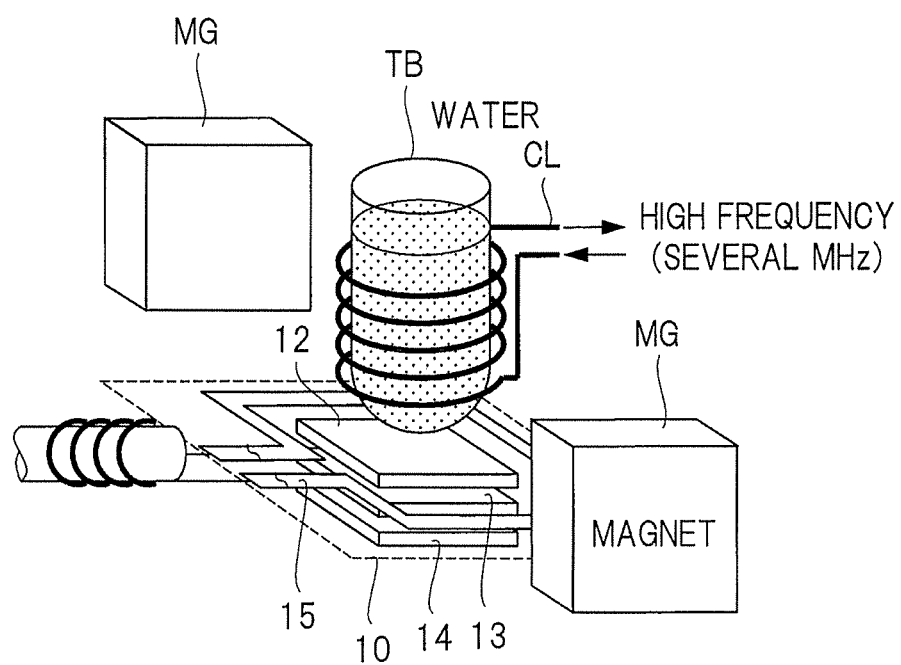
FIG. 14 is an explanatory drawing showing principles of a technique for measuring nuclear magnetization of water in a case where a magnetometer is applied according to a sixth embodiment.

FIG. 14 is an explanatory drawing showing principles of a technique for measuring nuclear magnetization of water in a case where the magnetometer is applied according to the sixth embodiment.

An excitation coil CL is wound around a test tube TB containing water. The test tube TB around which the excitation coil CL is wound is disposed between magnets MG. A DC static magnetic field caused by the magnets MG and a high-frequency magnetic field caused by the excitation coil CL are orthogonally applied to water in the test tube TB.

The magnetometer 10 is disposed in the vicinity of a bottom surface of the test tube TB. The magnetometer 10 is disposed in such a manner that a main surface of the magnetometer 10 is orthogonal to the high-frequency magnetic field caused by the excitation coil CL in order to obtain the highest sensitivity to a nuclear magnetization signal.

In the magnetometer 10, a microwave is supplied to the microwave coil 15 surrounding the diamond sensor 12a. In the magnetometer 10 shown in FIG. 14, the diamond sensor unit 12, the low-pass filter 13, and the photodiode 14 or the image sensor 41 are disposed closer to the test tube TB in the stated order. The excitation light is supplied to the diamond sensor 12a through the periphery of the diamond sensor unit 12, but the illustration thereof is omitted in FIG. 14.

<Example of Drive Timing in Measurement of Nuclear Magnetization of Water>

Next, an example of drive timing in measurement of nuclear magnetization of water will be described with reference to FIG. 15.

Figure 15:
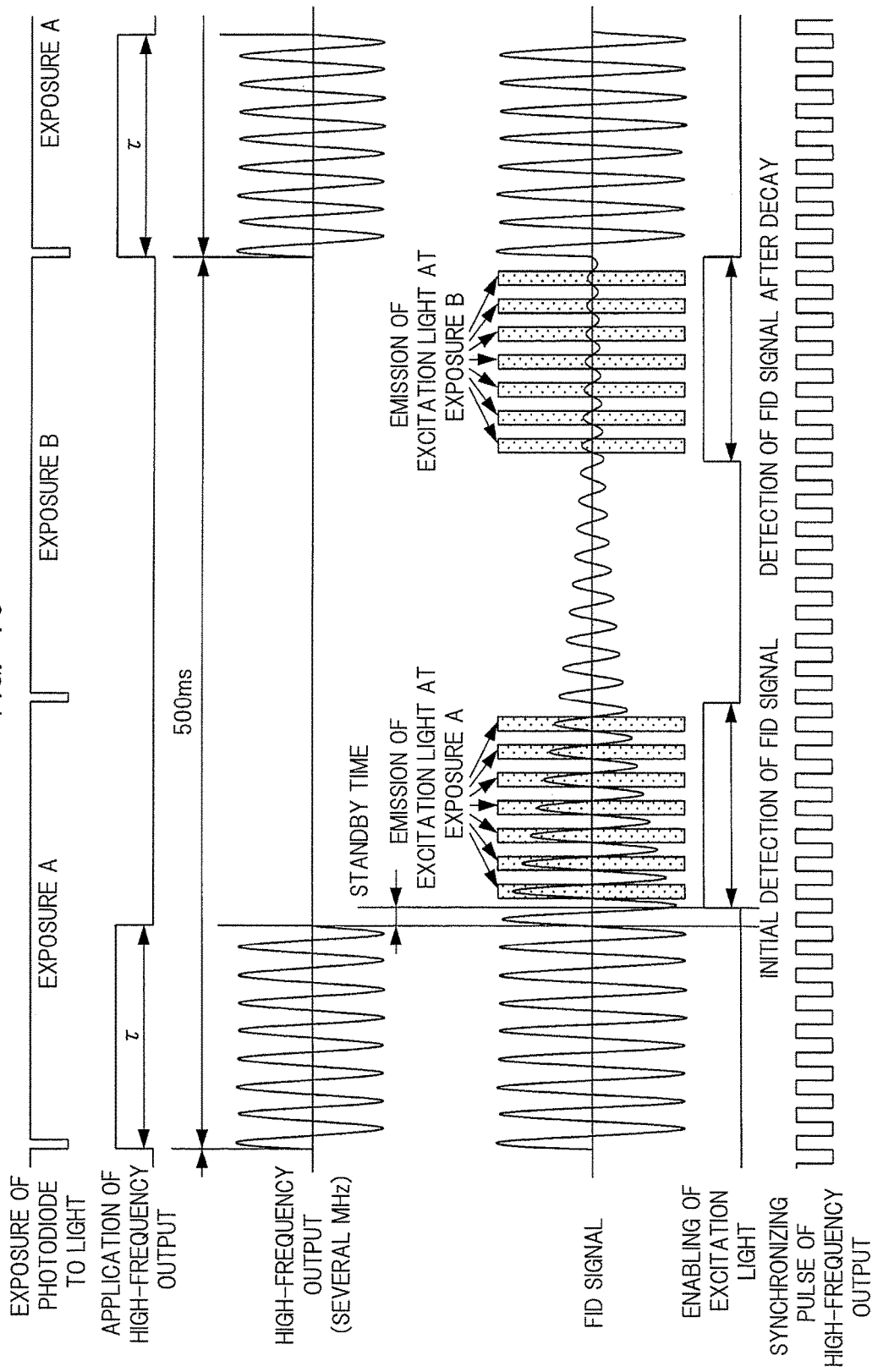
FIG. 15 is an explanatory drawing showing an example of drive timing in measurement of nuclear magnetization of water.

FIG. 15 is an explanatory drawing showing an example of drive timing in measurement of nuclear magnetization of water.

Since a relaxation time T1 of a water molecule is about several hundred milliseconds, each of application of a high-frequency output for an initial fixed time τ, initial detection of a free induction decay (FID) signal, and detection of the FID signal after decay is carried out in a cycle of, for example, 500 milliseconds.

More specifically, in order to carry out the initial detection of an FID signal and the detection of the FID signal after decay, a cycle of 500 milliseconds is divided into a first half and a latter half, and a photodiode is exposed to light in an exposure A and an exposure B. Then, after a standby time of a few milliseconds elapses after the application of a high-frequency output for an initial fixed time τ, excitation light is enabled only for a time of initial detection within the timing for the exposure A.

In addition, excitation light is enabled also after decay within the timing for the exposure B. Excitation light is controlled so as to be emitted only when an enable signal is in an on-state and a synchronizing pulse of a high-frequency output is in a positive phase.

Accordingly, an average value of amplitude of the FID signal in initial detection timing can be obtained as a photodiode output in the exposure A. Also, an average value of amplitude of the FID signal in detection timing after decay can be obtained as a photodiode output in the exposure B.

In this regard, the initial fixed time τ is:

$$\tau = \pi/(2\gamma B),$$

where $\gamma = e/m =$ electron charge/mass of nuclei of hydrogen, and B=intensity of magnetic field caused by a high-frequency output in water contained in a test tube. Also, the initial fixed time τ is referred to as a π/2 pulse.

After the π/2 pulse is applied, nuclear magnetization energy stored in a water molecule is induced and emitted, so that the FID signal is detected in the magnetometer 10.

By comparing the FID signal after application of the π/2 pulse and before the decay with the FID signal after the decay, it is possible to measure the relaxation time T1 of water. Since the relaxation time T1 of water reflects a temperature of water, the temperature of water can be measured in a noncontact manner.

At this time, a frequency F of a high-frequency output has a relationship of F/B0=42.57 [MHz/tesla] with the static magnetic field B0 which is applied to water in the test tube by magnets, and is referred to as the Larmor frequency.

In this measurement technique, LC resonance of inductance L of an excitation coil and a different capacitance is not used, and thus wide frequency-range measurement can be achieved with a varying frequency. Even in a case where the static magnetic field B0 in a sample, which is water in the test tube TB in FIG. 14 in this embodiment, is not constant, the measurement of nuclear magnetization is possible by setting the frequency F corresponding to a value of the static magnetic field B0.

By allowing the static magnetic field B0 to have a distribution, nuclear magnetization signals positionally distributed in a sample can be separately measured.

<Method of Setting Operation Point>

Next, an operation point on optically detected magnetic resonance (ODMR) used in measurement of nuclear magnetization of water will be described with reference to FIG. 16.

Figure 16:
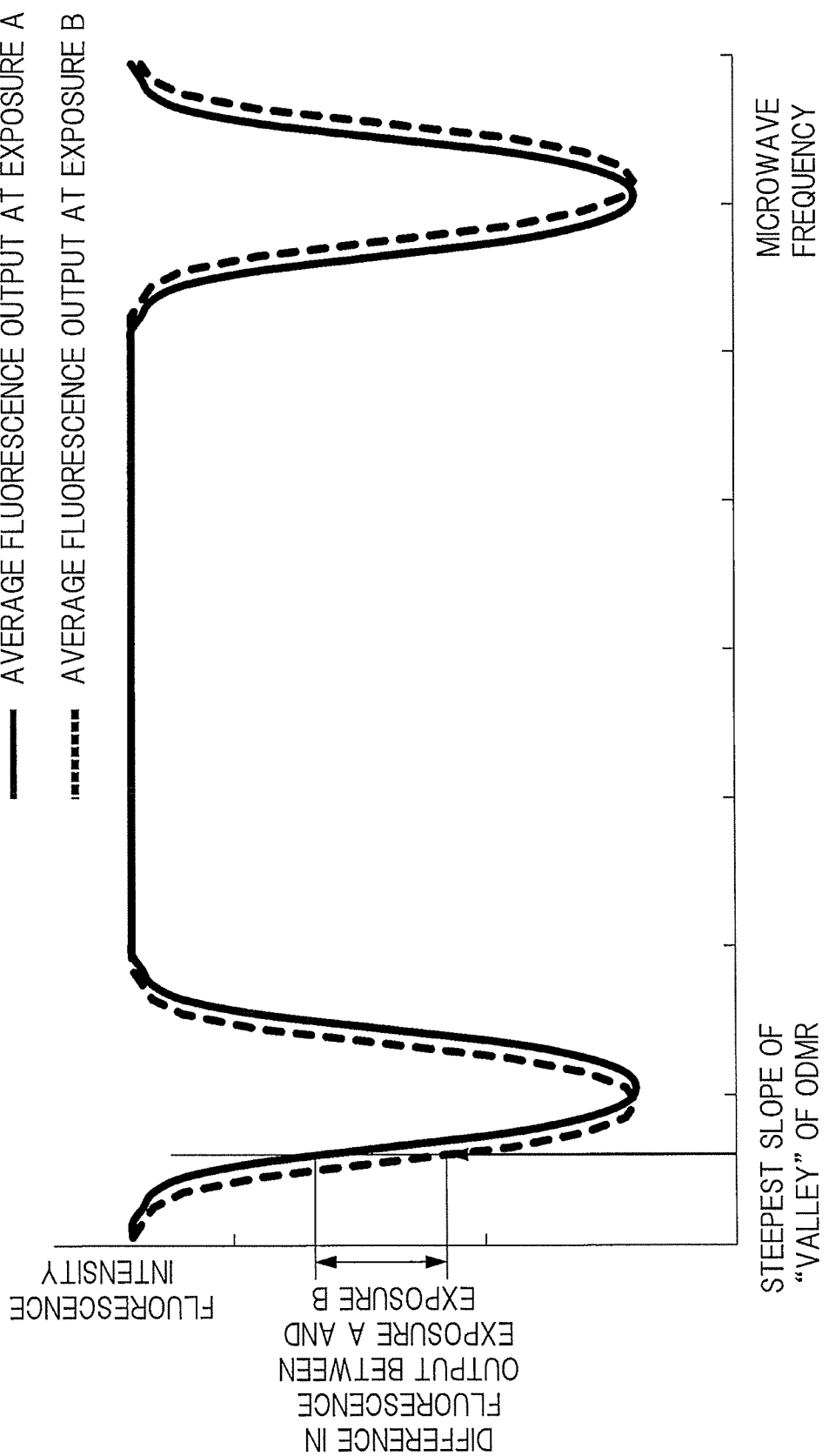
FIG. 16 is an explanatory drawing showing an operation point on ODMR used in measurement of nuclear magnetization of water.

FIG. 16 is an explanatory drawing showing the operation point on ODMR used in the measurement of nuclear magnetization of water.

In FIG. 16, a vertical axis represents fluorescence intensity of a diamond sensor, and a horizontal axis represents a frequency of a microwave applied onto the diamond sensor. Variation in fluorescence intensity which depends on the frequency of the microwave is referred to as ODMR.

In a state where a static magnetic field is not applied, a "valley" of fluorescence intensity is located in the vicinity of 2.87 GHz. Then, as application of the static magnetic field B0 proceeds, the position f of the "valley" on the frequency axis varies while maintaining the relationship represented by (Formula 1).

An operation point is set at the steepest slope of the "valley" in the static magnetic field B0. With respect to the operation point like this, an average of fluorescence output in the exposure A which reflects an average value of amplitude of an FID signal in initial detection timing and an average of fluorescence output in the exposure B which reflects an average value of the FID signal in detection timing after decay are shown as variation in ODMR in FIG. 16. A difference in fluorescence intensity is caused between before and after the decay of the FID signal. By measuring this difference, intensity of a nuclear magnetization signal can be measured.

Seventh Embodiment

<Overview>

In a seventh embodiment, an example in which measurement of a nuclear magnetization signal of water by the magnetometer 10 is applied to a non-invasive cooking home appliance will be described.

<Example of Application of Magnetometer to Cooking Home Appliance>

Figure 17B:
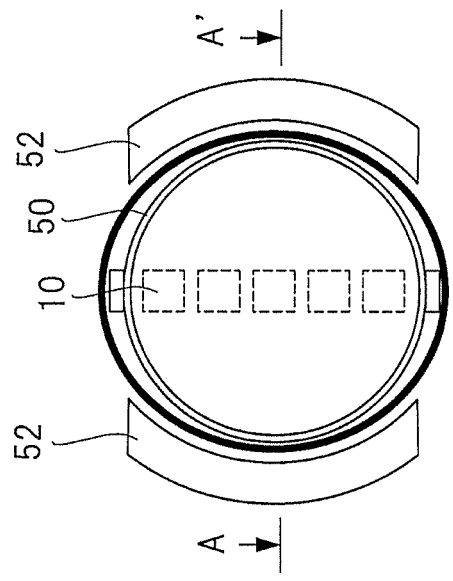
FIG. 17B is an explanatory drawing showing the example of the cooking household appliance using the magnetometer according to the seventh embodiment.
Figure 17C:
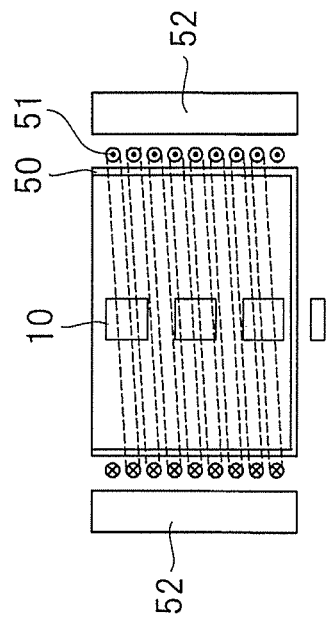
FIG. 17C is an explanatory drawing showing the example of the cooking household appliance using the magnetometer according to the seventh embodiment.
Figure 17A:
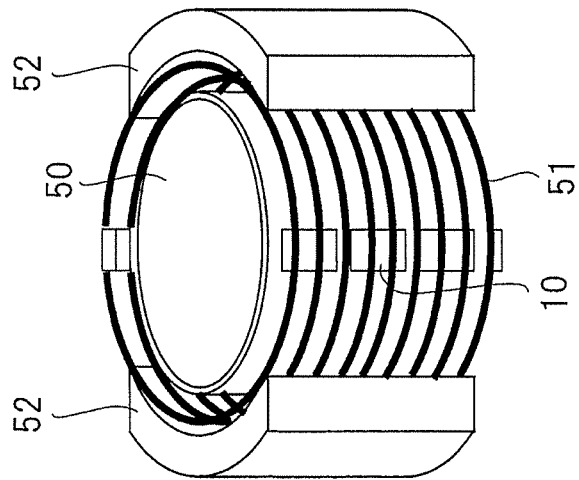
FIG. 17A is an explanatory drawing showing an example of a cooking household appliance using a magnetometer according to a seventh embodiment.

FIG. 17A to FIG. 17C are explanatory drawings showing an example of a cooking home appliance using the magnetometer 10 according to the seventh embodiment. FIG. 17A is a perspective view of the cooking home appliance. FIG. 17B is a plan view of FIG. 17A, and FIG. 17C is a cross-sectional view of a section A-A' in FIG. 17B.

The cooking home appliance is a cooking appliance used in, for example, a cooking process in which foodstuffs containing water are heated. As shown in FIG. 17A to FIG. 17C, the cooking home appliance includes a controlled heating container 50 having one end surface as a bottom surface and a shape of a hollow cylinder. The magnetometers 10 are linearly provided on the bottom surface and a side surface of the controlled heating container 50 at equal intervals so as to be orthogonal to a circumferential direction of the controlled heating container 50.

Also, the excitation coil 51 is provided in an outer periphery of the controlled heating container 50, and arc-shaped magnets 52 are provided on opposite sides of the controlled heating container 50 outside the excitation coil 51.

The controlled heating container 50 is non-magnetic and non-metallic, and is made of ceramic or the like. The controlled heating container 50 is a container in which foodstuffs containing water are put. A high-frequency current with the frequency F is applied to the excitation coil 51. The frequency F is set so that the frequency F and the static magnetic field B0 applied by magnets can establish a relationship of F/B0=42.57 [MHz/tesla].

After a high-frequency current of the above-stated π/2 pulse is applied to the excitation coil 51, the FID signals before and after the decay are measured by the magnetometer 10, so that a temperature in the controlled heating container 50 can be measured.

The FID signal from a water molecule is two-dimensionally radiated and is clearly detectable by the magnetometer 10 located at a close range. Accordingly, by arranging the magnetometers 10 around the controlled heating container 50, the temperature distribution in the controlled heating container 50 can be measured.

The excitation coil 51 can be used also as a heating coil. While a portion of water where the frequency F and the static magnetic field B0 establish a relationship of F/B0=42.57 [MHz/tesla] therebetween is heated, a distribution is caused to some extent in the static magnetic field in the controlled heating container 50. Thus, by adjusting the frequency F, it is possible to adjust a heating position.

Since the measurement of amplitude of the FID signal shown in FIG. 15 does not use LC resonance, there is no problem if the frequency F varies. To form a uniform magnetic field in the controlled heating container 50 requires a large magnet and incurs a high cost. However, the cooking home appliance shown in FIG. 17A to 17C does not require a large magnet.

Also, when the excitation coil 51 is used as a heating coil, a temperature distribution in the controlled heating container 50 is uniform in a circumferential direction during a heating process. Accordingly, an internal temperature distribution can be measured by arranging the magnetometers 10 one-dimensionally.

In the above-described manner, a cooking home appliance which is compact and efficient can be attained.

Eighth Embodiment

<Overview>

In an eighth embodiment, an example in which measurement of nuclear magnetization of water by the magnetometer 10 is applied to a health care device will be described.

<Example of Structure of Health Care Device>

FIG. 18A to FIG. 18C are explanatory drawings showing an example of a health care device using the magnetometer 10 according to the eighth embodiment. FIG. 18A is an explanatory drawing showing an example of perspective illustration of the health care device, and FIG. 183 is a cross-sectional view of FIG. 18A. FIG. 18C is a cross-sectional view of a section A-A' in FIG. 18B.

The health care device is health care equipment used in so-called thermotherapy such as hyperthermia. As shown in FIG. 18A, in the health care device, the plurality of magnetometers 10 are densely disposed so as to surround a trunk 60 of a human body which is an object of controlled heating. For example, the magnetometers 10 are sewn into clothes that an object person wears.

Also, an excitation coil 61 is wound around an area where the magnetometers 10 are densely disposed, and a pair of magnets 62 is disposed outside the excitation coil 61 so as to be opposite to each other.

A high-frequency current with the frequency F is applied to the excitation coil 61. The frequency F is set so that the frequency F and the static magnetic field B0 applied by the magnets can establish a relationship of F/B0=42.57 [MHz/tesla] at a portion where controlled heating is carried out for a trunk of a human body.

After a high-frequency current of the above-stated π/2 pulse is applied to the excitation coil 61, the FID signals before and after the decay are measured by the magnetometers 10, so that a temperature of the trunk 60 of a human body can be measured.

The FID signal from a water molecule is two-dimensionally radiated and is clearly detectable by a magnetic sensor module located at a close range. Accordingly, by arranging the magnetometers 10 around the trunk 60 of a human body, the temperature distribution in the trunk 60 of a human body can be measured.

The excitation coil 61 can be used also as a heating coil. While a portion of water where the frequency F and the static magnetic field B0 establish a relationship of F/B0=42.57 [MHz/tesla] therebetween is heated, the static magnetic field in the trunk 60 of a human body has a distribution to some extent. Thus, by adjusting the frequency F, it is possible to adjust a heating position.

In a case where it is necessary to more finely control the heating position, for example, radiation from the microwave coil 15 in the magnetometer 10 shown in FIG. 1 can be utilized. By supplying microwaves which are synchronized with each other and have the same frequency to a large number of magnetometers 10 and adjusting respective phases to adjust interference, electric power can be concentrated on a specific point in the trunk 60 of a human body with pinpoint accuracy based on principles of a phased array antenna.

In the above-described manner, the magnetometer 10 is effectively applicable to health care such as hyperthermia.

Also, the magnetometer 10 which is modularized and reduced in thickness is effectively applicable to a wearable diagnosis device which detects information about a body.

The magnetometer 10 which is modularized and reduced in thickness gives little feeling of oppression and allows weight reduction even if the magnetometers 10 are arranged densely on a surface of a human body. As a result, it is possible to reduce a burden on a patient who wears the wearable diagnosis device.

Ninth Embodiment

<Overview>

According to the above-described first to fifth embodiments, the microwave coil 15 is provided outside the diamond sensor unit 12. In a ninth embodiment, an example in which a microwave coil is provided within the diamond sensor case 12b will be described.

<Example of Structure of Magnetometer>

Figure 19:
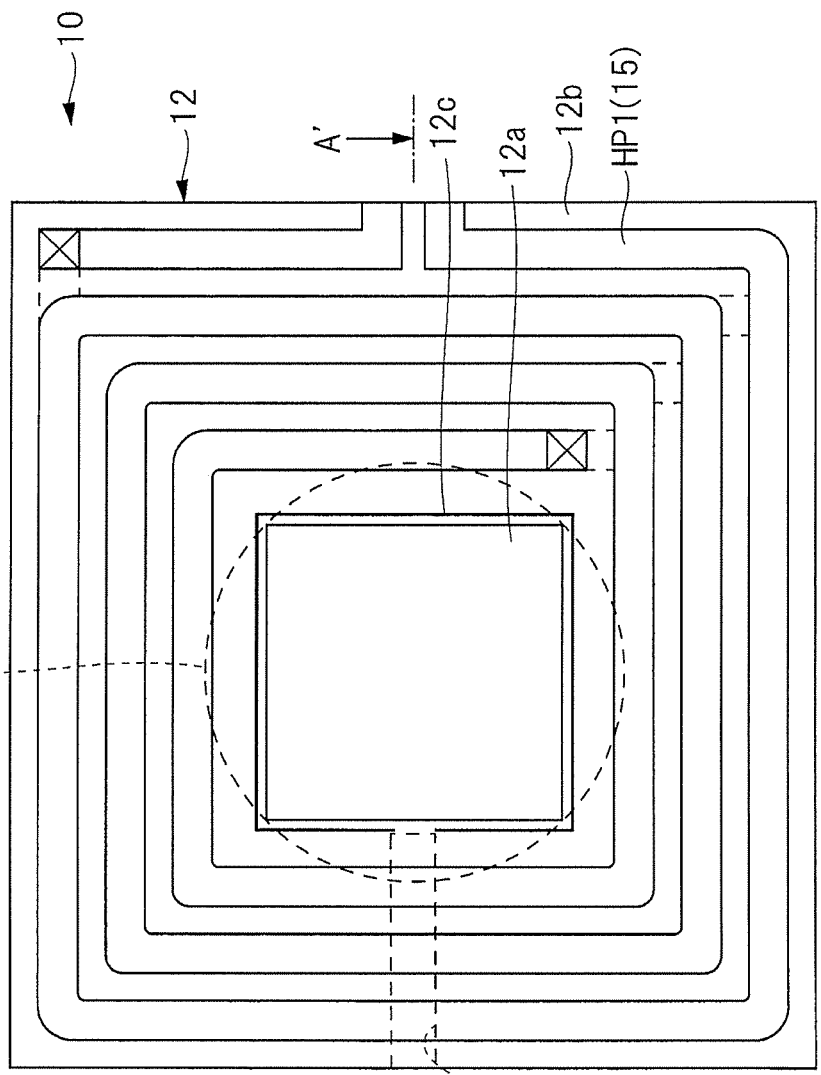
FIG. 19 is an explanatory drawing showing an example of a structure of a diamond sensor unit included in a magnetometer according to a ninth embodiment.
Figure 20:
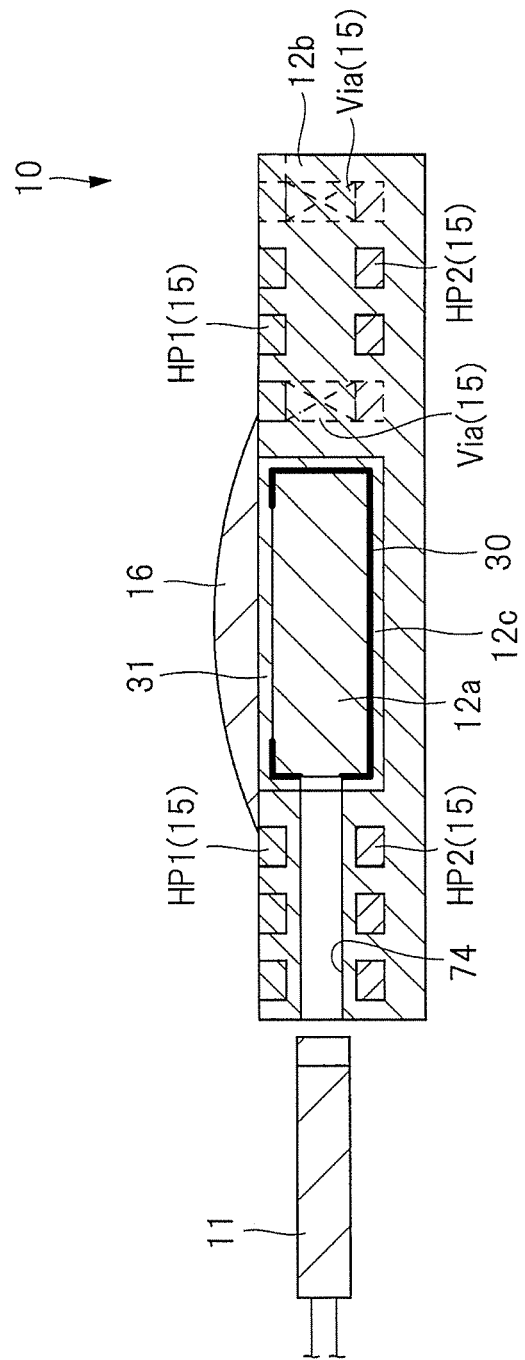
FIG. 20 is an explanatory drawing showing an example of a section A-A' in FIG. 19.

FIG. 19 is an explanatory drawing showing an example of a structure of a diamond sensor unit included in a magnetometer according to the ninth embodiment. FIG. 20 is an explanatory drawing showing an example of a section A-A' in FIG. 19.

In addition, in FIG. 19 and FIG. 20, only the diamond sensor unit 12 and the excitation light source 11 are shown for simplification, and the other elements including the low-pass filter 13, the photodiode 14, the lens 17, the signal processing circuit 18, the microwave circuit 19, and the control circuit 20 are omitted.

A difference between the magnetometer 10 shown in FIG. 19 and FIG. 20 and the magnetometer 10 shown in FIG. 1 and the like lies in a structure of the diamond sensor case 12b included in the diamond sensor unit 12. As shown in FIG. 19 and FIG. 20, the diamond sensor case 12b includes a diamond sensor storage 12c and the microwave coil 15.

The diamond sensor storage 12c is a cavity in which the diamond sensor 12a is stored, and is formed in a central portion of the diamond sensor case 12b. The microwave coil 15 is provided around the diamond sensor storage 12c.

As shown in FIG. 20, the microwave coil 15 is formed of a wiring pattern HP1 and a wiring pattern HP2 which are made of copper foil or the like. The wiring pattern HP1 is a wiring pattern formed at the uppermost level, that is, a wiring pattern formed on a back surface of the diamond sensor case 12b. The wiring pattern HP2 is a wiring pattern formed below the wiring pattern HP1.

The wiring pattern HP1 and the wiring pattern HP2 are connected to each other by a via Via. The via Via is formed by forming a via hole through the diamond sensor case and filling the via hole with a metal material such as copper, and electrically connects the wiring pattern HP1 formed at an upper level and the wiring pattern HP2 formed at a level below the wiring pattern HP1.

The excitation light source 11 is provided in the vicinity of a certain side surface of the diamond sensor unit 12. An excitation light path 74 is formed in the diamond sensor case 12b. The excitation light path 74 is an optical path along which excitation light is emitted from the excitation light source 11.

The excitation light path 74 is a hole which is formed so as to penetrate from the side where the excitation light source 11 is provided to the side where the diamond sensor storage 12c is formed. The excitation light path 74 is formed so as to be interposed between the wiring pattern HP1 and the wiring pattern HP2.

The fluorescence output window 31 is a window through which fluorescence generated by the diamond sensor 12a is output, and is formed on the back surface side opposite to the magnetism measurement surface which is the main surface of the diamond sensor 12a in the diamond sensor case 12b like the case shown in FIG. 1. The lens 16 is provided on the fluorescence output window 31.

The reflection film 30 is formed on the front surface of the diamond sensor storage 12c formed in the diamond sensor case 12b. Also in this example, the reflection film 30 is not formed in the opening for the excitation light path 74 and the fluorescence output window 31. The reflection film 30 is a metal film made of, for example, titanium, copper, aluminum or the like.

As described above, by the structure in which the microwave coil 15 is formed within the diamond sensor case 12b, the whole of the magnetometer 10 can be made smaller and thinner.

<Another Example of Structure of Magnetometer>

Figure 21:
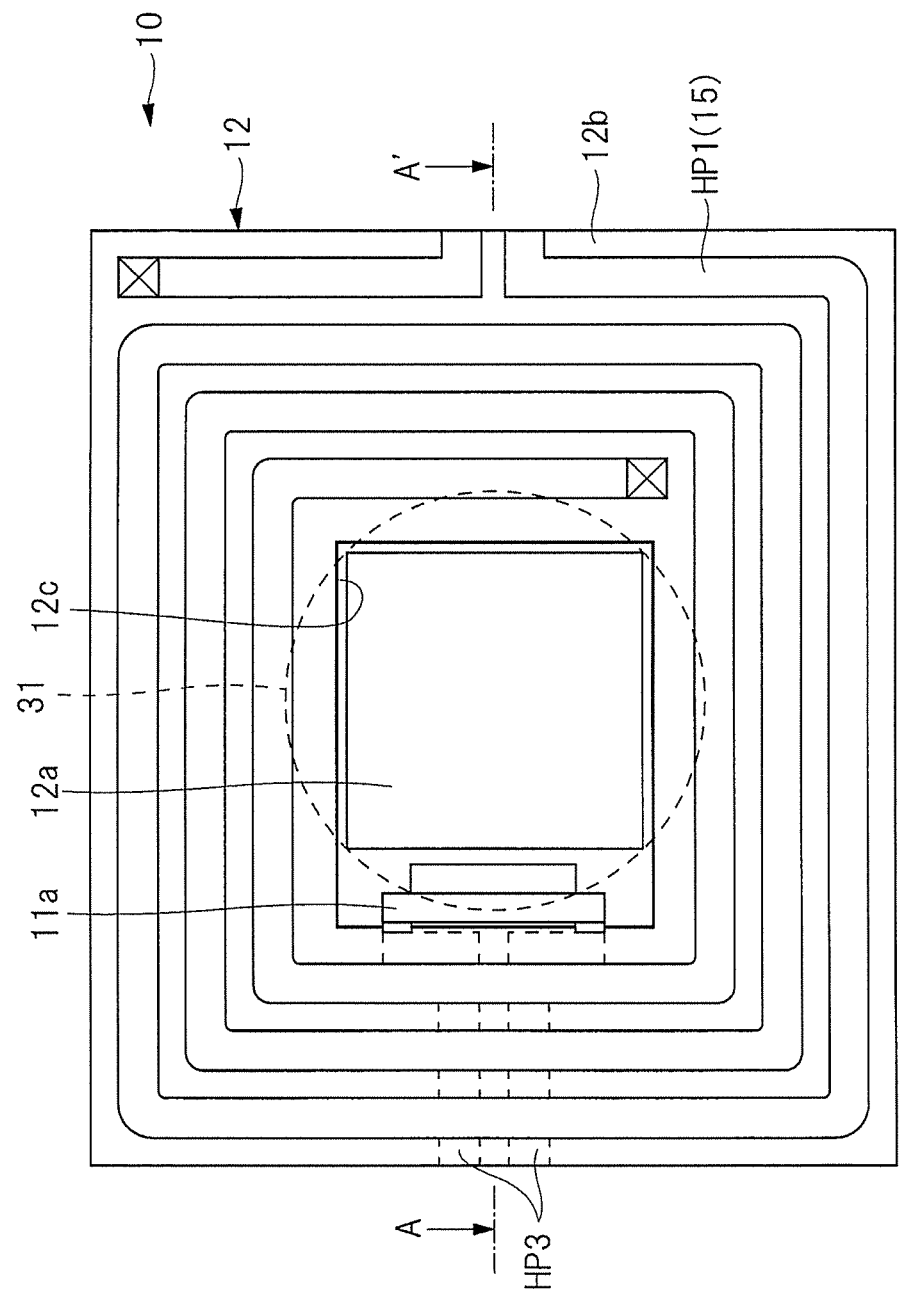
FIG. 21 is an explanatory drawing showing another example of the structure of the magnetometer shown in FIG. 19.

FIG. 21 is an explanatory drawing showing another example of the structure of the magnetometer shown in FIG. 19. Also, FIG. 22 is an explanatory drawing showing an example of a section A-A' in FIG. 21.

Figure 22:
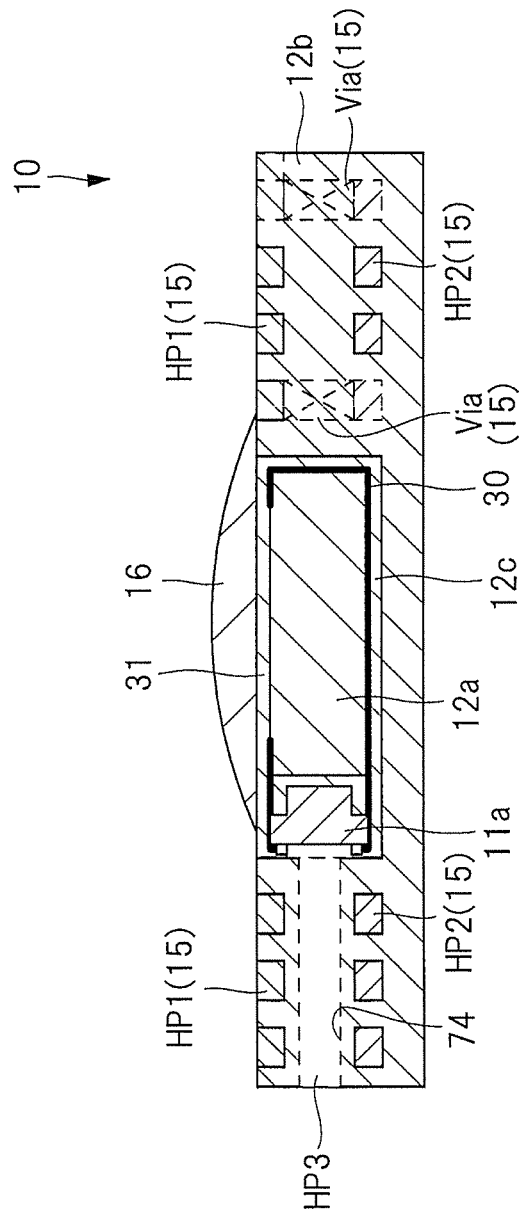
FIG. 22 is an explanatory drawing showing an example of a section A-A' in FIG. 21.

In FIG. 21 and FIG. 22, only the diamond sensor unit 12 is shown for simplification, and the other elements including the low-pass filter 13, the photodiode 14, the lens 17, the signal processing circuit 18, the microwave circuit 19, and the control circuit 20 are omitted.

The difference between the magnetometer 10 shown in FIG. 21 and FIG. 22 and the magnetometer 10 shown in FIG. 19 and FIG. 20 lies in that an excitation light source 11a as well as the microwave coil 15 is provided in the diamond sensor case 12b included in the diamond sensor unit 12.

In this case, the excitation light source 11a is formed of, for example, a surface-mount light emitting diode (LED), and is stored in the diamond sensor storage 12c together with the diamond sensor 12a. The excitation light source 11a irradiates a certain side surface of the diamond sensor 12a with excitation light.

A power supply wiring pattern HP3 is formed between the wiring pattern HP1 and the wiring pattern HP2 formed at a lower level. The power supply wiring pattern HP3 is a wiring pattern which supplies a power supply voltage supplied from the control circuit 20 or the like in FIG. 1 to the excitation light source 11a. Also in this example, the reflection film 30 is not formed in the portion corresponding to the fluorescence output window 31. The other structure is similar to that in FIG. 19 and FIG. 20, and thus description thereof is omitted.

As described above, by providing the excitation light source 11a as well as the microwave coil 15 within the diamond sensor case 12b, the magnetometer 10 can be made much smaller and much thinner.

In the foregoing, the invention made by the inventors of the present invention has been concretely described based on the embodiments. However, it is needless to say that the present invention is not limited to the foregoing embodiments and various modifications and alterations can be made within the scope of the present invention.

Note that the present invention is not limited to the embodiments described above and includes various modification examples. For examples, the embodiments above have been described in detail so as to make the present invention easily understood, and the present invention is not always limited to the embodiment having all of the described constituent elements.

Also, a part of the configuration of one embodiment may be replaced with the configuration of another embodiment, and the configuration of one embodiment may be added to the configuration of another embodiment. Furthermore, another configuration may be added to apart of the configuration of each embodiment, and apart of the configuration of each embodiment may be eliminated or replaced with another configuration.

What is claimed is:

1. A magnetometer which detects intensity of a magnetic field based on variation in fluorescence intensity, the magnetometer comprising:
   a diamond sensor including a plurality of nitrogen-vacancy centers;
   a diamond sensor case in which the diamond sensor is disposed;
   a reflection film reflecting excitation light and disposed on either a front surface or an inner surface of the diamond sensor case;
   an excitation light source which irradiates the diamond sensor in the diamond sensor case with the excitation light; and
   a fluorescence intensity detecting unit which detects the fluorescence intensity based on fluorescence from the diamond sensor case,
   wherein the diamond sensor case includes:
   a fluorescence output window through which the fluorescence occurring in the diamond sensor is output; and
   an excitation-light reception window through which the excitation light emitted by the excitation light source is received by the diamond sensor, and
   the fluorescence intensity detecting unit is disposed above a second main surface of the diamond sensor opposite to a first main surface of the diamond sensor, the first main surface being a magnetism measurement surface of the diamond sensor.

2. The magnetometer according to claim 1,
   wherein the diamond sensor further includes four side surfaces each connecting the first and second main surfaces to each other,
   the excitation-light reception window is disposed at a position where at least one of the four side surfaces of the diamond sensor is irradiated with the excitation light, and
   the excitation light source irradiates the excitation-light reception window with the excitation light.

3. The magnetometer according to claim 2, further comprising:
   a control circuit which controls operations of the excitation light source,
   wherein a plurality of excitation-light reception windows are provided on the diamond sensor case, and the control circuit controls the excitation light source so that each of the plurality of excitation-light reception windows is individually irradiated with the excitation light.

4. The magnetometer according to claim 1,
   wherein the excitation-light reception window is disposed at a position where at least one corner of the diamond sensor is irradiated with the excitation light, and
   the excitation light source irradiates the excitation-light reception window with the excitation light.

5. The magnetometer according to claim 4, further comprising:
   a control circuit which controls operations of the excitation light source,
   wherein a plurality of excitation-light reception windows are provided, and the control circuit controls the excitation light source so that each of the plurality of excitation-light reception windows is individually irradiated with the excitation light.

6. The magnetometer according to claim 1,
   wherein the excitation-light reception window is disposed at a position where the second surface of the diamond sensor is irradiated with the excitation light, and
   the excitation light source irradiates the excitation-light reception window with the excitation light.

7. The magnetometer according to claim 1, further comprising:
   a first lens which collects the fluorescence output from the diamond sensor case;
   a second lens which collects the fluorescence emitted from the first lens; and
   a low-pass filter which reflects the excitation light emitted by the excitation light source, and allows the fluorescence generated from the diamond sensor to pass and reach the fluorescence intensity detecting unit,
   wherein the low-pass filter is provided between the first lens and the second lens.

8. The magnetometer according to claim 1, wherein the reflection film is a metal film, and
   a thickness of the reflection film is smaller than a skin-effect depth at a frequency of a microwave applied to the diamond sensor case, and is larger than a skin-effect depth at a frequency of light.

9. The magnetometer according to claim 1,
   wherein the diamond sensor is a polycrystalline thin film.

10. The magnetometer according to claim 1,
    wherein the fluorescence intensity detecting unit is a photodiode.

11. The magnetometer according to claim 7,
    wherein the fluorescence intensity detecting unit is an image sensor including a plurality of pixels,
    each of the first and second lenses comprises a plurality of micro lenses, and
    each of the micro lenses is provided so as to correspond to one pixel or some pixels of the image sensor.

12. The magnetometer according to claim 11, further comprising:
    an optical path guide which suppresses scattering of the excitation light collected by the micro lenses included in the first lens,
    wherein the optical path guide is provided between the low-pass filter and the first lens.

13. The magnetometer according to claim 1,
    wherein the excitation light source is a semiconductor laser or an LED.

* * * * *